(12) United States Patent
Kato et al.

(10) Patent No.: US 6,348,141 B1
(45) Date of Patent: Feb. 19, 2002

(54) GAS SENSOR

(75) Inventors: Nobuhide Kato, Ama-gun; Nobukazu Ikoma; Yasuhiko Hamada, both of Nagoya, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/544,993

(22) Filed: Apr. 6, 2000

(30) Foreign Application Priority Data

Apr. 19, 1999 (JP) .......................................... 11-111242

(51) Int. Cl.[7] .......................................... G01N 27/407
(52) U.S. Cl. ........................ 204/428; 204/426; 204/427
(58) Field of Search ................................. 204/421–429

(56) References Cited

U.S. PATENT DOCUMENTS

| 4,272,349 | A | * | 6/1981 | Furutani et al. |
| 4,466,880 | A | * | 8/1984 | Torii et al. |
| 4,597,850 | A |   | 7/1986 | Takahasi et al. |
| 4,683,049 | A |   | 7/1987 | Nakajima et al. |
| 5,238,552 | A |   | 8/1993 | Kato et al. |
| 5,707,504 | A | * | 1/1998 | Jyouno et al. |

FOREIGN PATENT DOCUMENTS

| EP | 0 880 025 A1 | 11/1998 |
| JP | 1-169350 | 7/1989 |
| JP | 8-247995 | 9/1996 |
| JP | 8-271476 | 10/1996 |
| JP | 2641346 | 5/1997 |

* cited by examiner

Primary Examiner—T. Tung
(74) Attorney, Agent, or Firm—Burr & Brown

(57) ABSTRACT

A total of a most adjacent spacing distance in an axial direction between an outer gas-introducing hole of an outer protective cover and a slit provided at a flange of an intermediate protective cover and a most adjacent spacing distance in the axial direction between the slit of the intermediate protective cover and an inner gas-introducing hole of an inner protective cover is at least not less than 10 mm. Gaps for avoiding accumulation of water due to boundary tension are provided in a radial direction between the outer protective cover and the intermediate protective cover and in the radial direction between the outer protective cover and the inner protective cover.

7 Claims, 15 Drawing Sheets

FIG. 14

|  | SITUATION OF WATER SPLASH | CRACK |
|---|---|---|
| Comparative Example 1 | 10/10 | 2/10 |
| Comparative Example 2 | 0/10 | 0/10 |
| Working Example 1 | 3/10 | 0/10 |
| Working Example 2 | 2/10 | 0/10 |
| Working Example 3 | 0/10 | 0/10 |
| Working Example 4 | 1/10 | 0/10 |
| Working Example 5 | 1/10 | 0/10 |
| Working Example 6 | 3/10~4/10 | 0/10 |
| Working Example 7 | 3/10~4/10 | 0/10 |

GAS SENSOR

BACKGROUND OF THE INVENTION

1. Field of the Invention

The present invention relates to a gas sensor for measuring gas components such as NO, $NO_2$, $SO_2$, $CO_2$, and $H_2O$ contained, for example, in atmospheric air and exhaust gas discharged from vehicles or automobiles. In particular, the present invention relates to a gas sensor having a protective cover which is arranged to surround a sensor element.

2. Description of the Related Art

At present, a variety of gas sensors have been suggested and practically used, including, for example, oxygen sensors and NOx sensors based on the use of oxygen ion conductors (see Japanese Laid-Open Patent Publication No. 8-271476), HC sensors (see Japanese Laid-Open Patent Publication No. 8-247995), hydrogen sensors based on the use of proton ion conductors, $H_2O$ sensors, and oxygen sensors and various gas sensors based on the use of oxide conductors such as $SnO_2$ and $TiO_2$.

Among these gas sensors, the oxygen sensor based on the use of $ZrO_2$ and the oxygen sensor based on the use of $TiO_2$ keep stable performance even in an environment of exhaust gas discharged from the automobile. Therefore, they are widely used to control the oxygen concentration in the exhaust gas of the automobile and control A/F. The NOx sensor based on the use of $ZrO_2$ is also at a stage of practical use to control NOx for the automobile.

Those known as the oxygen sensor to be attached to an exhaust tube of an internal combustion engine include those having a protective cover which is intended to obtain a uniform flow of exhaust gas around a sensor element as described in Japanese Laid-Open Patent Publication No. 1-169350, and those having a protective cover which is intended to avoid any adhesion of condensed water (so-called water splash) caused when an engine is started. An oxygen sensor, which is attached with a protective cover having a double structure, is known as described in U.S. Pat. Nos. 4,597,850 and 4,683,049.

As for those having the conventional protective covers as described above, it is feared that the response performance may be slow in the case of the gas sensor provided with the protective cover which has the resistance to water scattering so that the water splash is prevented. Accordingly, a protective cover having the double structure has been suggested, wherein the response performance is improved such that an inner gas-introducing hole of an inner protective cover disposed adjacently to a sensor element is provided opposingly to the sensor element (see Japanese Patent No. 2641346).

However, the illustrative conventional structure described above is designed assuming that the sensor is installed on the upstream side of a catalyst. It has been revealed that when the sensor is used while it is installed on the downstream side of the catalyst, it causes a problem concerning the water scattering resistance (performance to avoid adhesion of condensed water caused when the engine is started).

As described above, when the structure of the protective cover is designed such that the input amount of the measurement gas is increased in order to obtain quick response, the condensed water, which is produced when the engine is started, tends to make invasion as well. In other words, the effect to prevent the sensor element from water splash is related to be contrary to the improvement in response performance. It is difficult to simultaneously satisfy these effects.

On the other hand, a cycle is assumed, in which the air-fuel ratio of exhaust gas is changed from the lean (atmosphere of excessive oxygen) to the theoretical air-fuel ratio or the rich, and the air-fuel ratio is returned again to the lean at a stage at which NOx is completely released from a catalyst, in order to reduce NOx occluded by the catalyst, when a NOx sensor having a function of oxygen sensor is attached on the downstream side of the NOx-absorbing catalyst. In such a case, if the complete release of NOx from the catalyst can be detected at an early stage, it is possible to decrease the unburned gas leaked from the catalyst.

SUMMARY OF THE INVENTION

The present invention has been made taking such problems into consideration, an object of which is to provide a gas sensor having a novel protective cover provided with resistance to water scattering, in which the gas diffusion rate-limiting can be decreased to be as small as possible, and the protective cover simultaneously satisfies both of high water scattering resistance and quick response performance.

The present invention lies in a gas sensor comprising a sensor element for measuring a predetermined gas component contained in an introduced measurement gas, and a protective cover arranged to surround the sensor element; wherein the protective cover includes an inner protective cover for covering at least a forward end portion of the sensor element; an outer protective cover for covering the inner protective cover; and an intermediate protective cover installed between the inner protective cover and the outer protective cover.

That is, the protective cover, which is used for the gas sensor according to the present invention, has a triple structure in which the intermediate protective cover is provided in the cover having a double structure composed of the inner protective cover and the outer protective cover. Therefore, it is possible to effectively avoid the adhesion of condensed water (so-called water splash) which would be otherwise caused when the engine is started. Further, it is possible to decrease the diffusion rate-limiting of the measurement gas as small as possible. Thus, it is possible to obtain quick response performance.

Accordingly, for example, when the gas sensor is attached on the downstream side of a NOx-absorbing catalyst to assume a cycle in which the air-fuel ratio of exhaust gas is changed from the lean to the theoretical air-fuel ratio or the rich, and the air-fuel ratio is returned again to the lean at a stage at which NOx is completely released from the catalyst, in order to reduce NOx occluded by the catalyst, then it is possible to detect the complete release of NOx from the catalyst at an early stage, and it is possible to decrease the unburned gas leaked from the catalyst.

In the gas sensor constructed as described above, the inner protective cover is formed to have a bottom-equipped cylindrical configuration with an inner gas-introducing hole which is formed at a position opposed to the sensor element and with an inner gas discharge hole which is formed at a bottom portion; the outer protective cover is formed to have a bottom-equipped cylindrical configuration with an outer gas-introducing hole which is disposed at a position not opposed to the inner gas-introducing hole of the inner protective cover; and the intermediate protective cover has an intermediate gas-introducing hole which is disposed at a position not opposed to the inner gas-introducing hole of the inner protective cover and the outer gas-introducing hole of the outer protective cover.

Accordingly, the water is introduced from the outer gas-introducing hole of the outer protective cover, most of which collides with the side surface of the intermediate protective cover and the side surface of the inner protective cover. The gas sensor is prevented from invasion of water into the inside. That is, the sensor element is prevented from invasion of water. The water is discharged to the outside without any delay through the outer gas-introducing hole of the outer protective cover.

Further, the measurement gas, which is introduced from the outer gas-introducing hole of the outer protective cover, passes through the intermediate gas-introducing hole of the intermediate protective cover and the inner gas-introducing hole of the inner protective cover, and it arrives at the sensor element. After that, the measurement gas is discharged through the gas discharge hole formed at the bottom portion of the inner protective cover and the outer gas-introducing hole of the outer protective cover. It is noted that the negative pressure is generated in the vicinity of the gas discharge hole disposed at the bottom of the inner protective cover. Therefore, the measurement gas flows quickly through the flow passage as described above. Accordingly, the diffusion rate-limiting of the measurement gas is decreased, and it is possible to obtain quick response performance.

It is preferable for the gas sensor constructed as described above that a total of a most adjacent spacing distance in an axial direction between the outer gas-introducing hole and the intermediate gas-introducing hole and a most adjacent spacing distance in the axial direction between the intermediate gas-introducing hole and the inner gas-introducing hole is at least not less than 10 mm. More preferably, the total is not less than 18 mm.

It is preferable that gaps for avoiding accumulation of water due to boundary tension are provided between the outer protective cover and the intermediate protective cover in a radial direction and between the outer protective cover and the inner protective cover in the radial direction.

It is also preferable for the gas sensor constructed as described above that the intermediate protective cover is formed to have a cylindrical configuration with an opening which is formed at a front portion thereof for inserting the inner protective cover thereinto and with a flange which is disposed at a rear portion thereof for making abutment against an inner wall of the outer protective cover. It is also preferable that the intermediate protective cover is formed to have a bottom-equipped cylindrical configuration with an intermediate gas discharge hole which is formed at a bottom portion thereof.

It is also preferable that a part of the outer gas-introducing hole of the outer protective cover is provided at a side surface portion of the outer protective cover between the inner gas discharge hole or the intermediate gas discharge hole and a bottom of the outer protective cover.

It is also preferable that the intermediate gas-introducing hole is formed at the flange of the intermediate protective cover.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 14 shows a table illustrating results of a second illustrative experiment (experiment to investigate the water scattering resistance)

DESCRIPTION OF THE PREFERRED EMBODIMENTS

Illustrative embodiments of the gas sensor according to the present invention will be explained below with reference to FIGS. 1 to 15.

Figure 1:
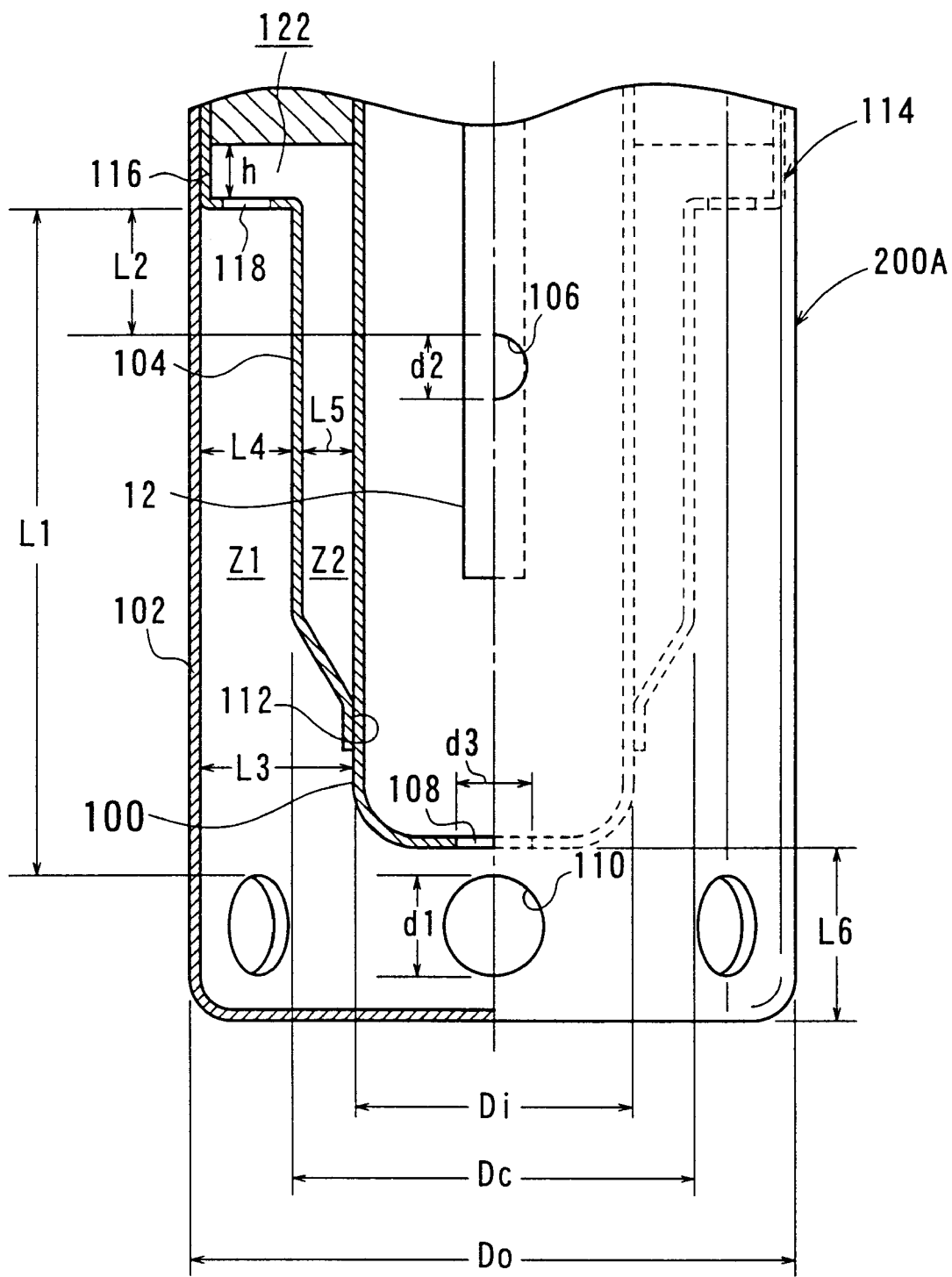
FIG. 1 shows a sectional view illustrating, with partial omission, a gas sensor according to an embodiment of the present invention attached with a protective cover concerning a first specified embodiment.

As shown in FIG. 1, a gas sensor according to an embodiment of the present invention comprises, for example, a sensor element 12 for measuring a predetermined gas component, for example, NOx contained in an introduced measurement gas (exhaust gas), and a protective cover 200A arranged to surround a forward end portion of the sensor element 12.

Figure 3:
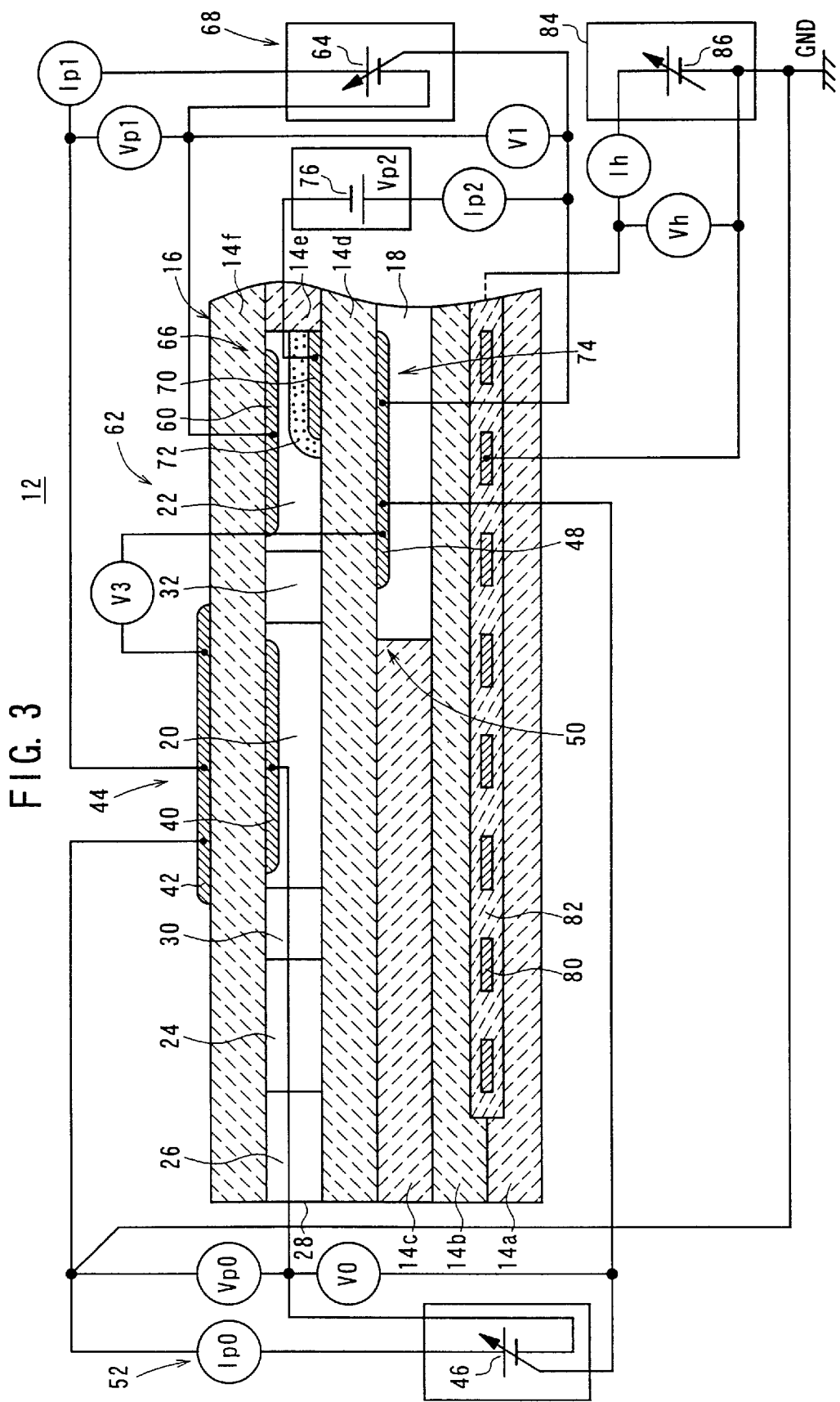
FIG. 3 shows a sectional view illustrating an example of a sensor element of the gas sensor according to the embodiment of the present invention.

As shown in FIG. 3, the sensor element 12 has a substrate 16 comprising, for example, six stacked solid electrolyte layers 14a to 14f composed of ceramics based on the use of oxygen ion-conductive solid electrolytes such as $ZrO_2$.

In the substrate 16, first and second layers from the bottom are designated as first and second substrate layers 14a, 14b respectively. Third and fifth layers from the bottom are designated as first and second spacer layers 14c, 14e respectively. Fourth and sixth layers from the bottom are designated as first and second solid electrolyte layers 14d, 14f respectively.

A space (reference gas-introducing space) 18, into which a reference gas such as atmospheric air to be used as a reference for measuring oxides is introduced, is formed between the second substrate layer 14b and the first solid electrolyte layer 14d, the space 18 being comparted by a lower surface of the first solid electrolyte layer 14d, an upper surface of the second substrate layer 14b, and side surfaces of the first spacer layer 14c.

A first chamber 20 for adjusting the partial pressure of oxygen in the measurement gas is formed and comparted between a lower surface of the second solid electrolyte layer 14f and an upper surface of the first solid electrolyte layer 14d. A second chamber 22 for finely adjusting the partial pressure of oxygen in the measurement gas and measuring oxides, for example, nitrogen oxides (NOx) in the measurement gas is formed and comparted between the lower surface of the second solid electrolyte layer 14f and the upper surface of the first solid electrolyte layer 14d.

The sensor element 12 comprises a buffering space 24 which is formed at the front end of the second spacer layer 14e. A first diffusion rate-determining section 26 is formed on the upstream side of the buffering space 24. A front end opening of the first diffusion rate-determining section 26 constitutes a gas-introducing port 28.

The buffering space 24 communicates with the first chamber 20 via a second diffusion rate-determining section 30. The first chamber 20 communicates with the second chamber 22 via a third diffusion rate-determining section 32. That is, the buffering space 24 is formed at the front end of the second spacer layer 14e, and it is comparted by the lower surface of the second solid electrolyte layer 14f, the upper surface of the first solid electrolyte layer 14d, the first diffusion rate-determining section 26, and the second diffusion rate-determining section 30.

The first, second, and third diffusion rate-determining sections 26, 30, 32 give predetermined diffusion resistances to the measurement gas introduced into the buffering space 24, the first chamber 20, and the second chamber 22 respectively. In this embodiment, each of them is formed as a slit which has a vertical length longer than a horizontal length and which has a predetermined cross-sectional area so that the measurement gas may be introduced thereinto. All of the vertically extending slits are formed at substantially central portions in the widthwise direction of the second spacer layer 14e.

A porous member composed of, for example, $ZrO_2$ may be charged and arranged in the slit of the third diffusion rate-determining section 32 so that the diffusion resistance of the third diffusion rate-determining section 32 may be larger than the diffusion resistance of the second diffusion rate-determining section 30. The diffusion resistance of the third diffusion rate-determining section 32 is preferably larger than that of the second diffusion rate-determining section 30. However, no problem occurs even when the former is smaller than the latter.

The atmosphere in the first chamber 20 is introduced into the second chamber 22 under the predetermined diffusion resistance via the third diffusion rate-determining section 32.

An inner pumping electrode 40 having a substantially rectangular planar configuration and composed of a porous cement electrode is formed on the entire lower surface portion for forming the first chamber 20, of the lower surface of the second solid electrolyte layer 14f. An outer pumping electrode 42 is formed on a portion corresponding to the inner pumping electrode 40, of the upper surface of the second solid electrolyte layer 14f. An electrochemical pumping cell, i.e., a main pumping cell 44 is constructed by the inner pumping electrode 40, the outer pumping electrode 42, and the second solid electrolyte layer 14f interposed between the both electrodes 40, 42.

A desired control voltage (pumping voltage) Vp0 is applied between the inner pumping electrode 40 and the outer pumping electrode 42 of the main pumping cell 44 by the aid of an external variable power source 46 to allow a pumping current Ip0 to flow in a positive or negative direction between the outer pumping electrode 42 and the inner pumping electrode 40. Thus, the oxygen in the atmosphere in the first chamber 20 can be pumped out to the external space, or the oxygen in the external space can be pumped into the first chamber 20.

A reference electrode 48 is formed on a lower surface portion exposed to the reference gas-introducing space 18, of the lower surface of the first solid electrolyte layer 14d. An electrochemical sensor cell, i.e., an oxygen partial pressure-detecting cell 50 is constructed by the inner pumping electrode 40, the reference electrode 48, the second solid electrolyte layer 14f, the second spacer layer 14e, and the first solid electrolyte layer 14d.

The oxygen partial pressure-detecting cell 50 is operated as follows. That is, an electromotive force is generated between the inner pumping electrode 40 and the reference electrode 48 on the basis of a difference in oxygen concentration between the atmosphere in the first chamber 20 and the reference gas (atmospheric air) in the reference gas-introducing space 18. The partial pressure of oxygen in the atmosphere in the first chamber 20 can be detected by using the electromotive force.

The detected value of the partial pressure of oxygen is used to feedback-control the variable power source 46. Specifically, the pumping operation effected by the main pumping cell 44 is controlled by the aid of a feedback control system 52 for the main pump so that the partial pressure of oxygen in the atmosphere in the first chamber 20 has a predetermined value which is sufficiently low to control the partial pressure of oxygen in the second chamber 22 in the next step.

The feedback control system 52 comprises a circuit constructed to feedback-control the pumping voltage Vp0 between the outer pumping electrode 42 and the inner pumping electrode 40 so that a difference (detection voltage V0) between an electric potential of the inner pumping electrode 40 and an electric potential of the reference electrode 48 is at a predetermined voltage level.

Therefore, the main pumping cell 44 pumps out or pumps in oxygen in an amount corresponding to the level of the pumping voltage Vp0, of the measurement gas introduced into the first chamber 20. The oxygen concentration in the first chamber 20 is subjected to feedback control to give a predetermined level by repeating the series of operations described above.

Each of the inner pumping electrode 40 and the outer pumping electrode 42 is composed of a porous cement electrode which is made of a metal such as Pt and a ceramic material such as $ZrO_2$. It is necessary to use a material which has a weak reducing ability or no reducing ability with respect to the NO component in the measurement gas, for the inner pumping electrode 40 disposed in the first chamber 20 to make contact with the measurement gas. It is preferable that the inner pumping electrode 40 is composed of, for example, a compound having the perovskite structure such as $La_3CuO_4$, a cement comprising a ceramic material and a metal such as Au having a low catalytic activity, or a cement comprising a ceramic material, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

On the other hand, an auxiliary pumping electrode 60 having a substantially rectangular planar configuration and composed of a porous cement electrode is formed on the entire lower surface portion for forming the second chamber 22, of the lower surface of the second solid electrolyte layer 14f. An auxiliary electrochemical pumping cell, i.e., an auxiliary pumping cell 62 is constructed by the outer pumping electrode 42 of the main pumping cell 44, the auxiliary pumping electrode 60, and the second solid electrolyte layer 14f.

A desired auxiliary control voltage Vp1 is applied between the outer pumping electrode 42 and the auxiliary pumping electrode 60 of the auxiliary pumping cell 62 by the aid of an external auxiliary variable power source 64. Thus, the oxygen in the atmosphere in the second chamber 22 can be pumped out to the external space, or the oxygen in the external space can be pumped into the second chamber 22.

An electrochemical sensor cell, i.e., an auxiliary oxygen partial pressure-detecting cell 66 is constructed by the auxiliary pumping electrode 60, the reference electrode 48, the second solid electrolyte layer 14f, the second spacer layer 14e, and the first solid electrolyte layer 14d. The auxiliary oxygen partial pressure-detecting cell 66 is operated as follows. That is, an electromotive force is generated between the auxiliary pumping electrode 60 and the reference electrode 48 on the basis of a difference in oxygen concentration between the atmosphere in the second chamber 22 and the reference gas (atmospheric air) in the reference gas-introducing space 18. The partial pressure of oxygen in the atmosphere in the second chamber 22 can be detected by using the electromotive force.

The detected value of the partial pressure of oxygen is used to feedback-control the auxiliary variable power source 64. Specifically, the pumping operation effected by the auxiliary pumping cell 62 is controlled by the aid of an auxiliary feedback control system 68 so that the partial pressure of oxygen in the atmosphere in the second chamber 22 has a low value of partial pressure of oxygen which does not sufficiently affect the measurement of the amount of the objective component under a condition in which the measurement gas component (NOx) is not substantially reduced or decomposed.

The feedback control system 68 comprises a circuit constructed to feedback-control the voltage (auxiliary control voltage) Vp1 between the outer pumping electrode 42 and the auxiliary pumping electrode 60 so that a difference (auxiliary detection voltage) V1 between an electric potential of the auxiliary pumping electrode 60 and an electric potential of the reference electrode 48 is at a predetermined voltage level.

Therefore, the auxiliary pumping cell 62 pumps out or pumps in oxygen in an amount corresponding to the level of the auxiliary control voltage Vp1, of the measurement gas introduced into the second chamber 22. The oxygen concentration in the second chamber 22 is subjected to feedback control to give a predetermined level by repeating the series of operations described above.

In this embodiment, owing to the operation of the main pumping cell 44 for the first chamber 20, the change in amount of oxygen introduced into the second chamber 22 is greatly reduced as compared with the change in the measurement gas. Accordingly, the partial pressure of oxygen in the second chamber 22 is accurately controlled to be constant.

In the sensor element 12, a detecting electrode 70 having a substantially rectangular planar configuration and composed of a porous cement electrode is formed at a portion separated from the third diffusion rate-determining section 32, on an upper surface portion for forming the second chamber 22, of the upper surface of the first solid electrolyte layer 14d. An alumina film for constructing a fourth diffusion rate-determining section 72 is formed so that the detecting electrode 70 is covered therewith. An electrochemical pumping cell, i.e., a measuring pumping cell 74 is constructed by the detecting electrode 70, the reference electrode 48, and the first solid electrolyte layer 14d.

The detecting electrode 70 is composed of a porous cement comprising zirconia as a ceramic material and Rh as a metal capable of reducing NOx as the measurement gas component. Accordingly, the detecting electrode 70 functions as a NOx-reducing catalyst for reducing NOx existing in the atmosphere in the second chamber 22. Further, the oxygen in the atmosphere in the second chamber 22 can be pumped out to the reference gas-introducing space 18 by applying a constant voltage Vp2 between the detecting electrode 70 and the reference electrode 48 by the aid of a DC power source (constant voltage power source) 76. The pumping current Ip2, which is allowed to flow in accordance with the pumping operation performed by the measuring pumping cell 74, is detected by an ammeter.

The constant voltage power source 76 can apply a voltage of a magnitude to give a limiting current to the pumping for oxygen produced during decomposition in the measuring pumping cell 74 under the inflow of NOx restricted by the fourth diffusion rate-determining section 72.

The sensor element 12 further comprises a heater 80 for generating heat in accordance with electric power supply from the outside. The heater 80 is embedded in a form of being vertically interposed between the first and second substrate layers 14a, 14b. The heater 80 is provided in order to increase the conductivity of oxygen ion. A ceramic layer 82 composed of alumina or the like is formed to cover upper and lower surfaces of the heater 80 so that the heater 80 is electrically insulated from the substrate layers 14a, 14b.

As shown in the drawing, the heater 80 is arranged over the entire portion ranging from the first chamber 20 to the second chamber 22. Each of the first chamber 20 and the second chamber 22 is heated to a predetermined temperature in accordance with the control effected by a heater output controller 84 connected to the heater 80. Simultaneously, each of the main pumping cell 44, the oxygen partial pressure-detecting cell 50, the auxiliary pumping cell 62, and the measuring pumping cell 74 is also heated to a predetermined temperature and maintained at that temperature. In this embodiment, a positive side lead wire of the heater 80 is connected to a heater power source 86 via the heater output controller 84, and a negative side lead wire of the heater 80 is grounded (GND).

In the sensor element 12, the outer pumping electrode 42 of the main pumping cell 44 is connected to the positive side lead wire of the heater 80.

Next, the operation of the sensor element 12 will be explained. At first, the forward end of the sensor element 12 is disposed in the external space. Accordingly, the measurement gas is introduced into the first chamber 20 under the predetermined diffusion resistance via the first diffusion rate-determining section 26, the buffering space 24, and the second diffusion rate-determining section 30. The measurement gas, which has been introduced into the first chamber 20, is subjected to the pumping action for oxygen, caused by applying the predetermined pumping voltage Vp0 between the outer pumping electrode 42 and the inner pumping electrode 40 which construct the main pumping cell 44. The partial pressure of oxygen is controlled to have a predetermined value, for example, $10^{-7}$ atm. The control is performed by the aid of the feedback control system 52.

The second diffusion rate-determining section 30 serves to limit the amount of diffusion and inflow of oxygen in the measurement gas into the measuring space (first chamber 20) when the pumping voltage Vp0 is applied to the main pumping cell 44 so that the current flowing through the main pumping cell 44 is suppressed.

In the first chamber 20, a state of partial pressure of oxygen is established, in which NO in the atmosphere is not reduced by the inner pumping electrode 40 even in an environment of being heated by the external measurement gas and being heated by the heater 80. For example, a condition of partial pressure of oxygen is formed, in which the reaction of $NO \rightarrow \frac{1}{2}N_2 + \frac{1}{2}O_2$ does not occur, because of the following reason. That is, if NO in the measurement gas (atmosphere) is reduced in the first chamber 20, it is impossible to accurately measure NOx in the second chamber 22 disposed at the downstream stage. In this context, it is necessary to establish a condition in the first chamber 20 in which NO is not reduced by the component which participates in reduction of NO (in this case, the metal component of the inner pumping electrode 40). However, it is also allowable that a part of NO is decomposed. Specifically, as described above, such a condition is achieved by using, for the inner pumping electrode 40, the material having a low ability to reduce NO, for example, an alloy of Au and Pt.

The gas in the first chamber 20 is introduced into the second chamber 22 under the predetermined diffusion resistance via the third diffusion rate-determining section 32. The gas, which has been introduced into the second chamber 22, is subjected to the pumping action for oxygen, caused by applying the auxiliary pumping voltage Vp1 between the outer pumping electrode 42 and the auxiliary pumping electrode 60 which constitute the auxiliary pumping cell 62 to make fine adjustment so that the partial pressure of oxygen has a constant and low value of partial pressure of oxygen.

The third diffusion rate-determining section 32 serves to limit the amount of diffusion and inflow of oxygen in the measurement gas into the measuring space (second chamber 22) when the auxiliary control voltage Vp1 is applied to the auxiliary pumping cell 62 so that the pumping current Ip1 flowing through the auxiliary pumping cell 62 is suppressed, in the same manner as performed by the second diffusion rate-determining section 30.

In the second chamber 22, a state of partial pressure of oxygen is established, in which NO in the atmosphere is not reduced by the auxiliary pumping electrode 60 in an environment of being heated by the external measurement gas and being heated by the heater 80. Accordingly, it is also necessary to use a material which has a weak reducing ability or no reducing ability with respect to the NO component in the measurement gas, for the auxiliary pumping electrode 60, in the same manner as for the inner pumping electrode 40. It is preferable that the auxiliary pumping electrode 60 is composed of, for example, a compound having the perovskite structure such as $La_3CuO_4$, a cement comprising a ceramic material and a metal such as Au having a low catalytic activity, or a cement comprising a ceramic material, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

The measurement gas, which has been controlled for the partial pressure of oxygen in the second chamber 22 as described above, is introduced into the detecting electrode 70 under the predetermined diffusion resistance via the fourth diffusion rate-determining section 72.

When it is intended to control the partial pressure of oxygen in the atmosphere in the first chamber 20 to have a low value of the partial pressure of oxygen which does not substantially affect the measurement of NOx, by operating the main pumping cell 44, in other words, when the pumping voltage Vp0 of the variable power source 46 is adjusted by the aid of the feedback control system 52 so that the voltage V0 detected by the oxygen partial pressure-detecting cell 50 is constant, if the oxygen concentration in the measurement gas greatly changes, for example, in a range of 0 to 20%, then the respective partial pressures of oxygen in the atmosphere in the second chamber 22 and in the atmosphere in the vicinity of the detecting electrode 70 slightly change in ordinary cases. This phenomenon is caused probably because of the following reason. That is, when the oxygen concentration in the measurement gas increases, the distribution of the oxygen concentration occurs in the widthwise direction and in the thickness direction in the first chamber 20. The distribution of the oxygen concentration changes depending on the oxygen concentration in the measurement gas.

However, in the case of the sensor element 12, the auxiliary pumping cell 62 is provided for the second chamber 22 so that the partial pressure of oxygen in its internal atmosphere always has a constant low value of the partial pressure of oxygen. Accordingly, even when the partial pressure of oxygen in the atmosphere introduced from the first chamber 20 into the second chamber 22 changes depending on the oxygen concentration in the measurement gas, the partial pressure of oxygen in the atmosphere in the second chamber 22 can be always made to have a constant low value, owing to the pumping action performed by the auxiliary pumping cell 62. As a result, the partial pressure of oxygen can be controlled to have a low value at which the measurement of NOx is not substantially affected.

NOx in the measurement gas introduced into the detecting electrode 70 is reduced or decomposed around the detecting electrode 70. Thus, for example, a reaction of $NO \rightarrow \frac{1}{2}N_2 + \frac{1}{2}O_2$ is allowed to occur. In this process, a predetermined voltage Vp2, for example, 430 mV is applied between the detecting electrode 70 and the reference electrode 48 which construct the measuring pumping cell 74, in a direction to pump out the oxygen from the second chamber 22 to the reference gas-introducing space 18.

Therefore, the pumping current Ip2 flowing through the measuring pumping cell 74 has a value which is proportional to a sum of the oxygen concentration in the atmosphere introduced into the second chamber 22, i.e., the oxygen concentration in the second chamber 22 and the oxygen concentration produced by reduction or decomposition of NOx by the aid of the detecting electrode 70.

In this embodiment, the oxygen concentration in the atmosphere in the second chamber 22 is controlled to be constant by means of the auxiliary pumping cell 62. Accordingly, the pumping current Ip2 flowing through the measuring pumping cell 74 is proportional to the NOx concentration. The NOx concentration corresponds to the amount of diffusion of NOx limited by the fourth diffusion rate-determining section 72. Therefore, even when the oxygen concentration in the measurement gas greatly changes, it is possible to accurately measure the NOx concentration, based on the use of the measuring pumping cell 74 by the aid of the ammeter.

According to the fact described above, almost all of the pumping current value Ip2 obtained by operating the measuring pumping cell 74 represents the amount brought about by the reduction or decomposition of NOx. Accordingly, the obtained result does not depend on the oxygen concentration in the measurement gas.

In the meantime, the sensor element 12 undergoes the exhaust gas pressure pulsation in the external space. As a result, the oxygen suddenly enters the sensor element 12 via the gas-introducing port 28. However, the oxygen from the external space does not directly enter the first chamber 20, but it enters the buffering space 24 disposed at the upstream stage thereof. That is, the sudden change in oxygen concentration, which is caused by the exhaust gas pressure pulsation, is counteracted by the buffering space 24. Thus, the influence of the exhaust gas pressure pulsation on the first chamber 20 is in an almost negligible degree.

As a result, the oxygen-pumping amount effected by the main pumping cell 44 for the first chamber 20 is well correlated with the oxygen concentration in the measurement gas, and it is possible to improve the measurement accuracy obtained by using the measuring pumping cell 74. Simultaneously, the controlling oxygen partial pressure-detecting cell can be commonly used, for example, as a sensor for determining the air-fuel ratio.

In this arrangement, the lean and the rich of the air-fuel ratio can be detected on the basis of the pumping current IpO of the main pumping cell 44. The stoichiometry of the air-fuel ratio can be detected on the basis of the voltage V3 between the outer pumping electrode 42 and the reference electrode 48.

Figure 4:
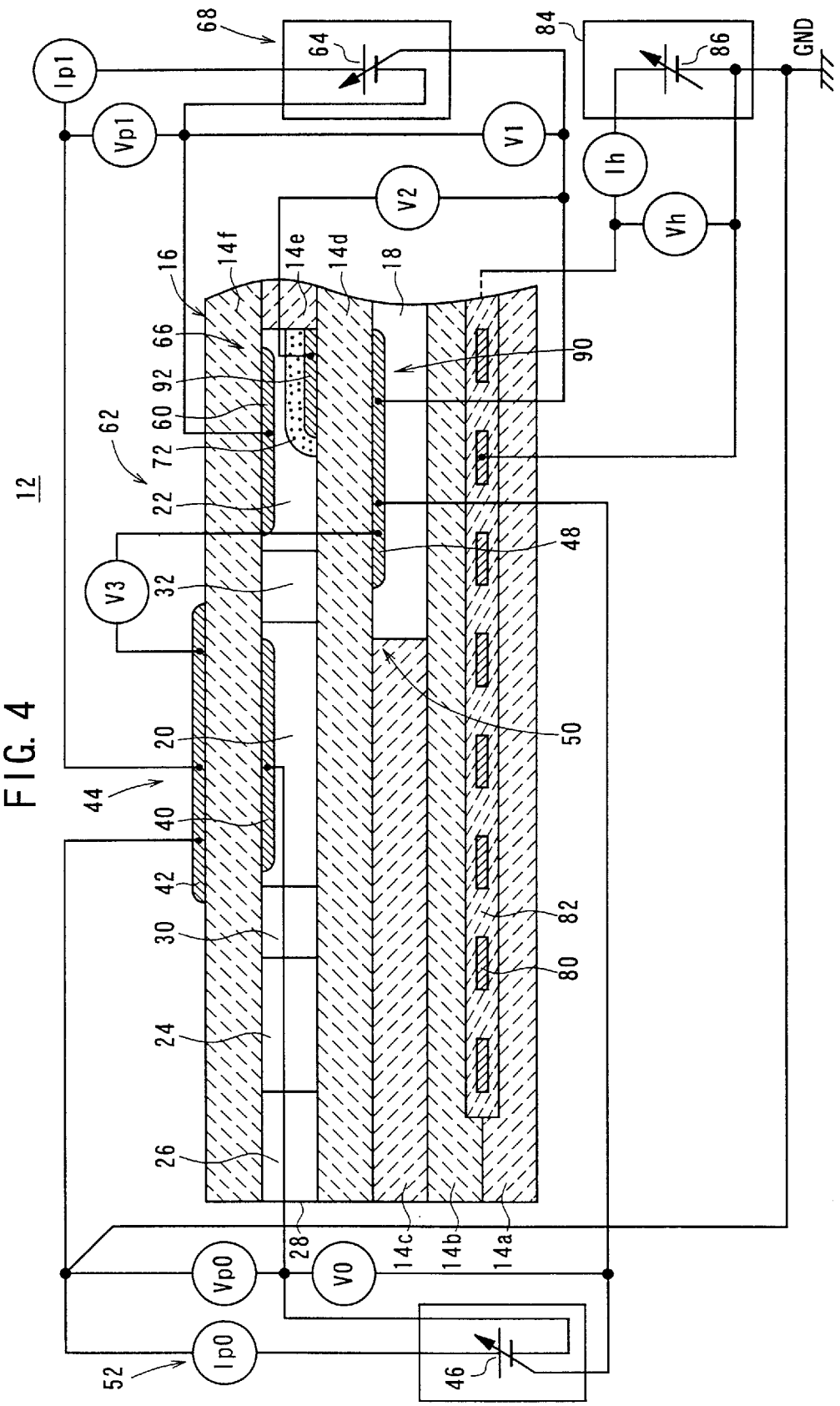
FIG. 4 shows a sectional view illustrating another example of a sensor element of the gas sensor according to the embodiment of the present invention.

The sensor element 12 may be constructed without using the measuring pumping cell 74. As shown in FIG. 4, a measuring oxygen partial pressure-measuring cell 90 may be used as an electrochemical sensor cell for detecting NOx in place of the measuring pumping cell 74.

The measuring oxygen partial pressure-measuring cell 90 comprises a detecting electrode 92 formed on an upper surface portion for forming the second chamber 22, of the upper surface of the first solid electrolyte layer 14d, the reference electrode 48 formed on the lower surface of the first solid electrolyte layer 14d, and the first solid electrolyte layer 14d.

In this embodiment, an electromotive force (electromotive force of an oxygen concentration cell) V2 corresponding to the difference in oxygen concentration between the atmosphere around the detecting electrode 92 and the atmosphere around the reference electrode 48 is generated between the reference electrode 48 and the detecting electrode 92 of the measuring oxygen partial pressure-measuring cell 90.

Therefore, the partial pressure of oxygen in the atmosphere around the detecting electrode 92, in other words, the partial pressure of oxygen defined by oxygen produced by reduction or decomposition of the measurement gas component (NOx) is detected as a voltage value V2 by measuring the electromotive force (voltage) V2 generated between the detecting electrode 92 and the reference electrode 48 by using a voltmeter.

The degree of the change of the electromotive force V2 represents the concentration of NOx. In other words, the electromotive force V2, which is outputted from the measuring oxygen partial pressure-measuring cell 90 constructed by the detecting electrode 92, the reference electrode 48, and the first solid electrolyte layer 14d, represents the concentration of NOx in the measurement gas.

Description of Protective Cover

As shown in FIG. 1, the protective cover 200A concerning a first specified embodiment, which is arranged to surround the sensor element 12, comprises an inner protective cover 100 for covering the forward end portion of the sensor element 12, an outer protective cover 102 for covering the inner protective cover 100, and an intermediate protective cover 104 installed between the inner protective cover 100 and the outer protective cover 102.

The inner protective cover 100 is made of metal, and it is formed to have a bottom-equipped cylindrical configuration. A plurality of inner gas-introducing holes 106 are formed at positions opposed to the sensor element 12. An inner gas discharge hole 108 is formed at the bottom (forward end portion).

The outer protective cover 102 is made of metal, and it is formed to have a bottom-equipped cylindrical configuration. The outer protective cover 102 has outer gas-introducing holes 110 at positions on its side circumferential surface not opposed to the inner gas-introducing holes 106 of the inner protective cover 100.

The intermediate protective cover 104 is made of metal, and it is formed to have a cylindrical configuration. An opening 112 for inserting the inner protective cover 100 therethrough is formed at its front portion. The intermediate protective cover 104 has, at its rear portion, a flange 114 which abuts against the inner wall of the outer protective cover 102.

The flange 114 has its rear end portion which is bent laterally to integrally form a bent section 116 bent rearwardly at its circumferential edge. The outer circumferential surface of the bent section 116 abuts against the inner wall of the outer protective cover 102.

Figure 2:
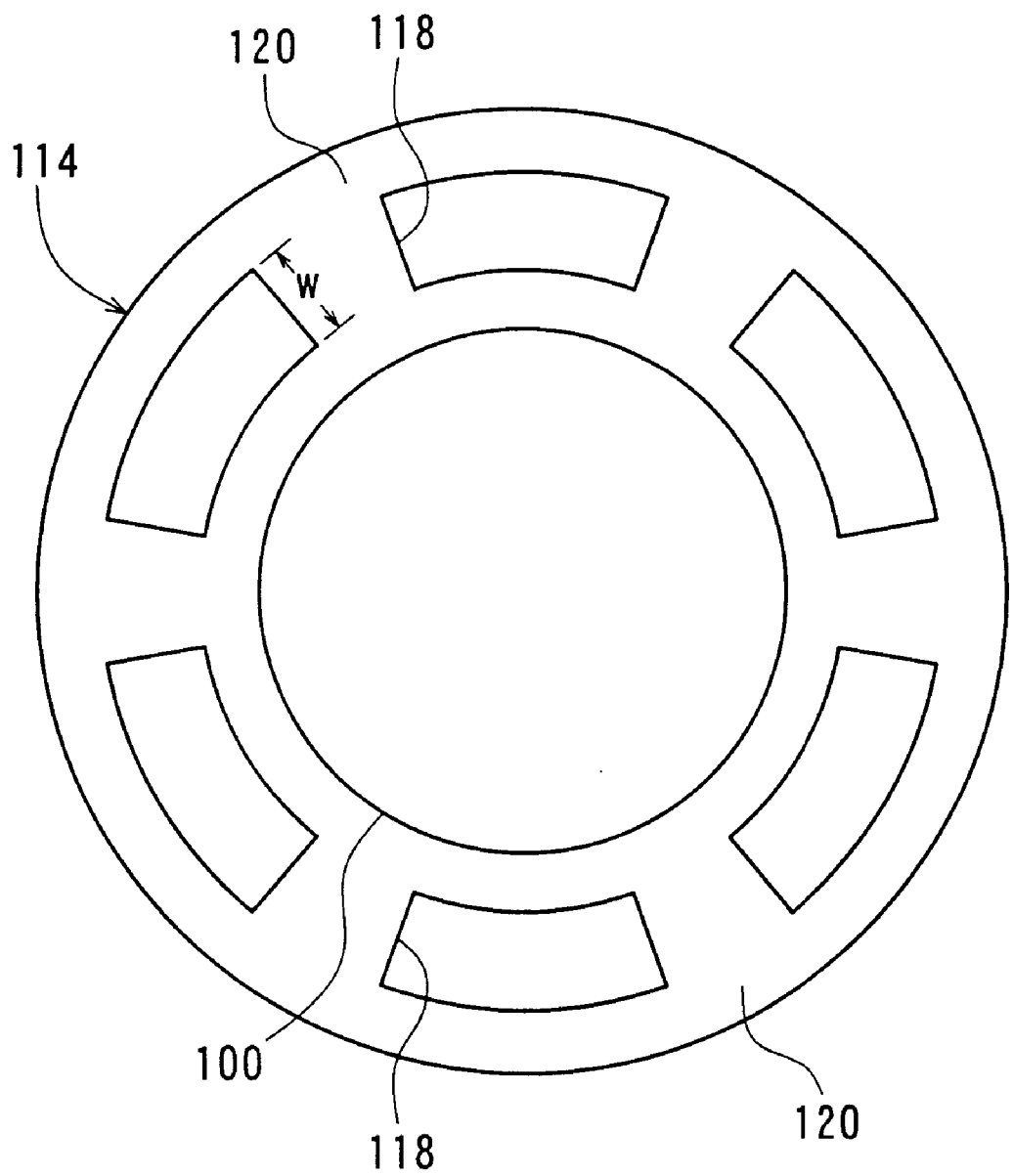
FIG. 2 shows an arrangement of a flange of a protective cover concerning a third specified embodiment, as viewed from a front end side of an inner protective cover.

As shown in FIG. 2, the flange 114 has, at its front circumferential surface, a plurality of slits 118 for constructing intermediate gas-introducing holes. In this embodiment, the slits 118, which are arranged at equally divided six positions, are formed. Each of the slits 118 has a circular arc-shaped configuration with a central angle of 40° with respect to the circumference of the flange 114. A circular arc-shaped gap 120 with a central angle of 20° is disposed between the adjoining slits 118.

The following dimensional relationship is preferred. That is, the total of the most adjacent spacing distance L1 in the axial direction between the outer gas-introducing hole 110 of the outer protective cover 102 and the intermediate gas-introducing hole (slit 118) of the intermediate protective cover 104 and the most adjacent spacing distance L2 in the axial direction between the intermediate gas-introducing hole (slit 118) of the intermediate protective cover 104 and the inner gas-introducing hole 106 of the inner protective cover 100 is at least not less than 10 mm, and preferably not less than 18 mm.

It is preferable to provide gaps for avoiding accumulation of water due to the boundary tension between the outer protective cover 102 and the intermediate protective cover 104 in the radial direction and between the outer protective cover 102 and the inner protective cover 100 in the radial direction.

In this embodiment, the dimension L3 of the gap Z1 between the outer protective cover 102 and the inner protective cover 100 is at least not less than 1.5 mm in the radial direction. The dimension L4 of the gap Z1 between the outer protective cover 102 and the intermediate protective cover 104 is at least not less than 1.5 mm. It is preferable that the dimension L5 of the gap Z2 between the intermediate protective cover 104 and the inner protective cover 100 is not less than 1 mm.

The distance L6 from the bottom of the outer protective cover 102 to the most adjacent gas discharge hole (inner gas discharge hole 108 in this embodiment) is at least not less than 1.5 mm, and preferably not less than 3 mm.

Further, as shown in FIG. 2, the width w in the radial direction of the slit 118 provided at the flange 114 of the intermediate protective cover 104 is 0.5 to 1.5 mm. As shown in FIG. 1, the height h of the gap formed at the inside of the bent section 116 is preferably not less than about 1.0 mm.

For example, the specified dimension of the protective cover 200A concerning the first specified embodiment is as follows. That is, as for the outer protective cover 102, the outer diameter Do of the outer protective cover 102 is about 14.2 mm. The outer gas-introducing holes 110 having a diameter d1=about 2.5 mm are arranged at equally divided six positions between the inner gas discharge hole 108 and the bottom of the outer protective cover 102, of the side circumferential surface of the outer protective cover 102. The thickness of the outer protective cover 102 is about 0.4 mm.

The inner protective cover 100 is made of metal, and it is formed to have a bottom-equipped cylindrical configuration. The outer diameter Di thereof is about 6.6 mm. The plurality of inner gas-introducing holes 106 are formed at portions opposed to the sensor element 12, of its side circumferential surface. In this embodiment, the inner gas-introducing holes 106 having a diameter d2=about 1.4 mm are arranged at equally divided six positions. One inner gas-introducing hole 106 of the six inner gas-introducing holes 106 is provided at a position opposed to the surface (surface of the second solid electrolyte layer 14f) on which the outer pumping electrode 42 of the sensor element 12 is formed. The diameter d3 of the inner gas discharge hole 108 provided at the bottom of the inner protective cover 100 is about 2.0 mm. The thickness of the inner protective cover 100 is about 0.3 mm.

As for the intermediate protective cover 104, the outer diameter Dc thereof is about 9.4 mm, and the thickness thereof is about 0.3 mm.

The most adjacent spacing distance L1 in the axial direction between the outer gas-introducing hole 110 and the intermediate gas-introducing hole (slit 118) is about 15.1 mm. The most adjacent spacing distance L2 in the axial direction between the intermediate gas-introducing hole (slit 118) and the inner gas-introducing hole 106 is about 3.3 mm. The total of the most adjacent spacing distance L1 in the axial direction between the outer gas-introducing hole 110 and the intermediate gas-introducing hole (slit 118) and the most adjacent spacing distance L2 in the axial direction between the intermediate gas-introducing hole (slit 118) and the inner gas-introducing hole 106 is about 18.4 mm.

The dimension L4 in the radial direction of the gap Z1 between the outer protective cover 102 and the intermediate protective cover 104 is about 2 mm. The dimension L3 in the radial direction of the gap Z1 between the outer protective cover 102 and the inner protective cover 100 is about 3.4 mm.

The dimension L5 in the radial direction of the gap Z2 between the intermediate protective cover 104 and the inner protective cover 100 is about 1.1 mm. The distance L6 from the bottom of the outer protective cover 102 to the inner gas discharge hole 108 is about 4 mm.

The width w in the radial direction of the slit 118 provided at the flange 114 of the intermediate protective cover 104 is about 1.0 mm. The height h of the gap 122 formed at the inside of the bent section 116 is about 1.2 mm.

As described above, the protective cover 200A concerning the first specified embodiment has the triple structure in which the intermediate protective cover 104 is provided for the protective cover having the double structure composed of the inner protective cover 100 and the outer protective cover 102. Therefore, it is possible to effectively avoid the adhesion of condensed water (so-called water splash) which would be otherwise caused when the engine is started.

The water is introduced through the outer gas-introducing hole 110 of the outer protective cover 102, most of which collides with the side surface of the intermediate protective cover 104 and the side surface of the inner protective cover 100. The inside of the gas sensor 10 is prevented from invasion of water. That is, the sensor element 12 is prevented from invasion of water. The water is discharged to the outside without any delay through the outer gas-introducing hole 110 of the outer protective cover 102.

Further, the measurement gas, which is introduced through the outer gas-introducing hole 110 of the outer protective cover 102, passes through the intermediate gas-introducing hole (slit 118) of the intermediate protective cover 104 and the inner gas-introducing hole 106 of the inner protective cover 100, and it arrives at the sensor element 12. After that, the measurement gas is discharged through the inner gas discharge hole 108 formed at the bottom of the inner protective cover 100 and the outer gas-introducing hole 110 of the outer protective cover 102. The negative pressure is produced in the vicinity of the inner gas discharge hole 108 at the bottom of the inner protective cover 100. Therefore, the measurement gas quickly flows through the flow passage described above. As a result, the diffusion rate-limiting is decreased for the measurement gas, and it is possible to obtain quick response performance.

Accordingly, when the gas sensor 10 is attached on the downstream side of a NOx-absorbing catalyst to assume a cycle in which the air-fuel ratio of exhaust gas is changed from the lean to the theoretical air-fuel ratio or the rich, and the air-fuel ratio is returned again to the lean at a stage at which NOx is completely released from the catalyst, in order to reduce NOx occluded by the catalyst, then it is possible to detect the complete release of NOx from the catalyst at an early stage, and it is possible to decrease the unburned gas leaked from the catalyst.

Next, a protective cover 200B concerning a second specified embodiment will be explained with reference to FIG. 5. Components or parts corresponding to those shown in FIG. 1 are designated by the same reference numerals, duplicate explanation of which will be omitted.

Figure 5:
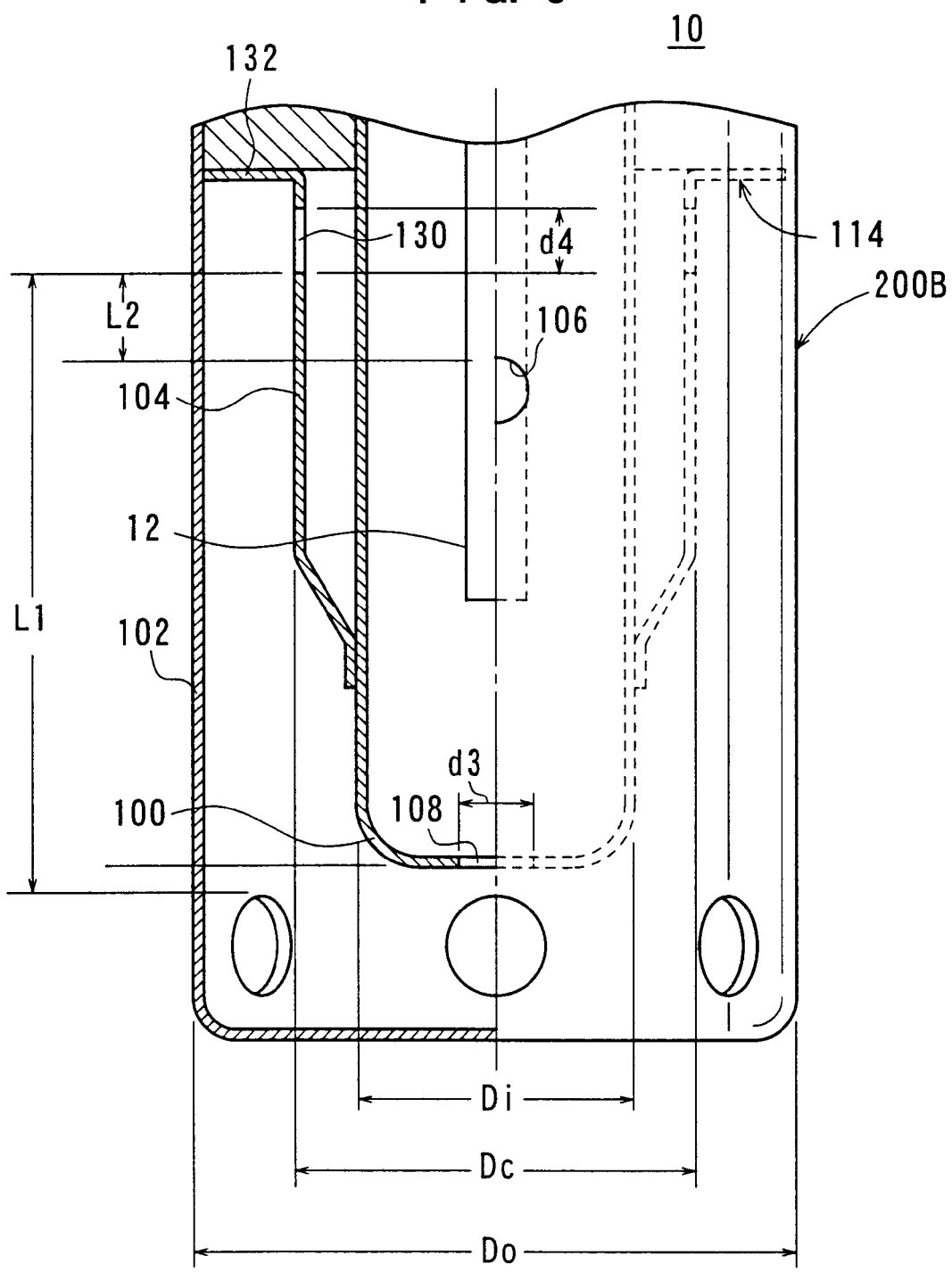
FIG. 5 shows a sectional view illustrating, with partial omission, a gas sensor according to an embodiment of the present invention attached with a protective cover concerning a second specified embodiment.

As shown in FIG. 5, the protective cover 200B concerning the second specified embodiment is constructed in approximately the same manner as the protective cover 200A concerning the first specified embodiment. However, the former is different from the latter in that intermediate gas-introducing holes 130 are formed at positions not opposed to the inner gas-introducing holes 106 of the inner protective cover 100 and the outer gas-introducing holes 110 of the outer protective cover 102, at the side circumferential surface of the intermediate protective cover 104, and that the flange 114 is composed of a plate member 132 which is bent laterally.

The respective intermediate gas-introducing holes 130 have a diameter d4=about 1.4 mm, and they are arranged at equally divided six positions.

The most adjacent spacing distance L1 in the axial direction between the outer gas-introducing hole 110 and the intermediate gas-introducing hole 130 is about 14.1 mm. The most adjacent spacing distance L2 in the axial direction between the intermediate gas-introducing hole 130 and the inner gas-introducing hole 106 is about 2.4 mm.

Also in the protective cover 200B concerning the second specified embodiment, it is possible to effectively avoid the adhesion of condensed water (so-called water splash) which would be otherwise caused when the engine is started. Further, the diffusion rate-limiting of the measurement gas can be decreased to be as small as possible, and it is possible to obtain quick response performance.

Next, a protective cover 200C concerning a third specified embodiment will be explained with reference to FIG. 6. Components or parts corresponding to those shown in FIG. 1 are designated by the same reference numerals, duplicate explanation of which will be omitted.

Figure 6:
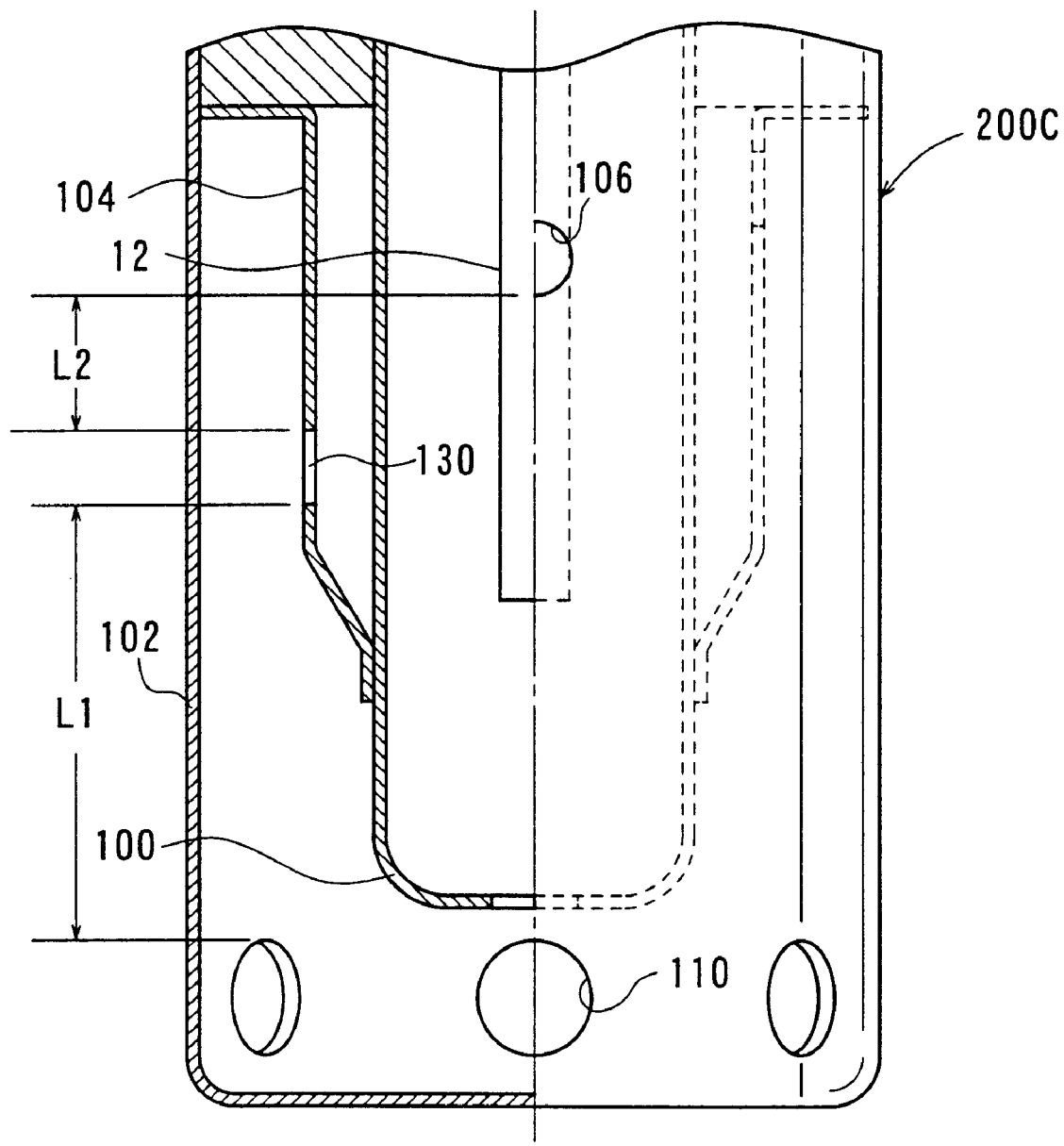
FIG. 6 shows a sectional view illustrating, with partial omission, a gas sensor according to an embodiment of the present invention attached with a protective cover concerning a third specified embodiment.

As shown in FIG. 6, the protective cover 200C concerning the third specified embodiment is constructed in approximately the same manner as the protective cover 200B concerning the second specified embodiment. However, the former is different from the latter in that intermediate gas-introducing holes 130 are formed at positions deviated from the position of formation of the inner gas-introducing hole 106 toward the bottom of the outer protective cover 102.

The most adjacent spacing distance L1 in the axial direction between the outer gas-introducing hole 110 and the intermediate gas-introducing hole 130 is about 7.9 mm. The most adjacent spacing distance L2 in the axial direction between the intermediate gas-introducing hole 130 and the inner gas-introducing hole 106 is about 3.0 mm.

Also in this case, it is possible to effectively avoid the adhesion of condensed water (so-called water splash) which would be otherwise caused when the engine is started. Further, the diffusion rate-limiting of the measurement gas can be decreased to be as small as possible, and it is possible to obtain quick response performance.

Next, a protective cover 200D concerning a fourth specified embodiment will be explained with reference to FIGS. 7 and 8. Components or parts corresponding to those shown in FIG. 6 are designated by the same reference numerals, duplicate explanation of which will be omitted.

Figure 7:
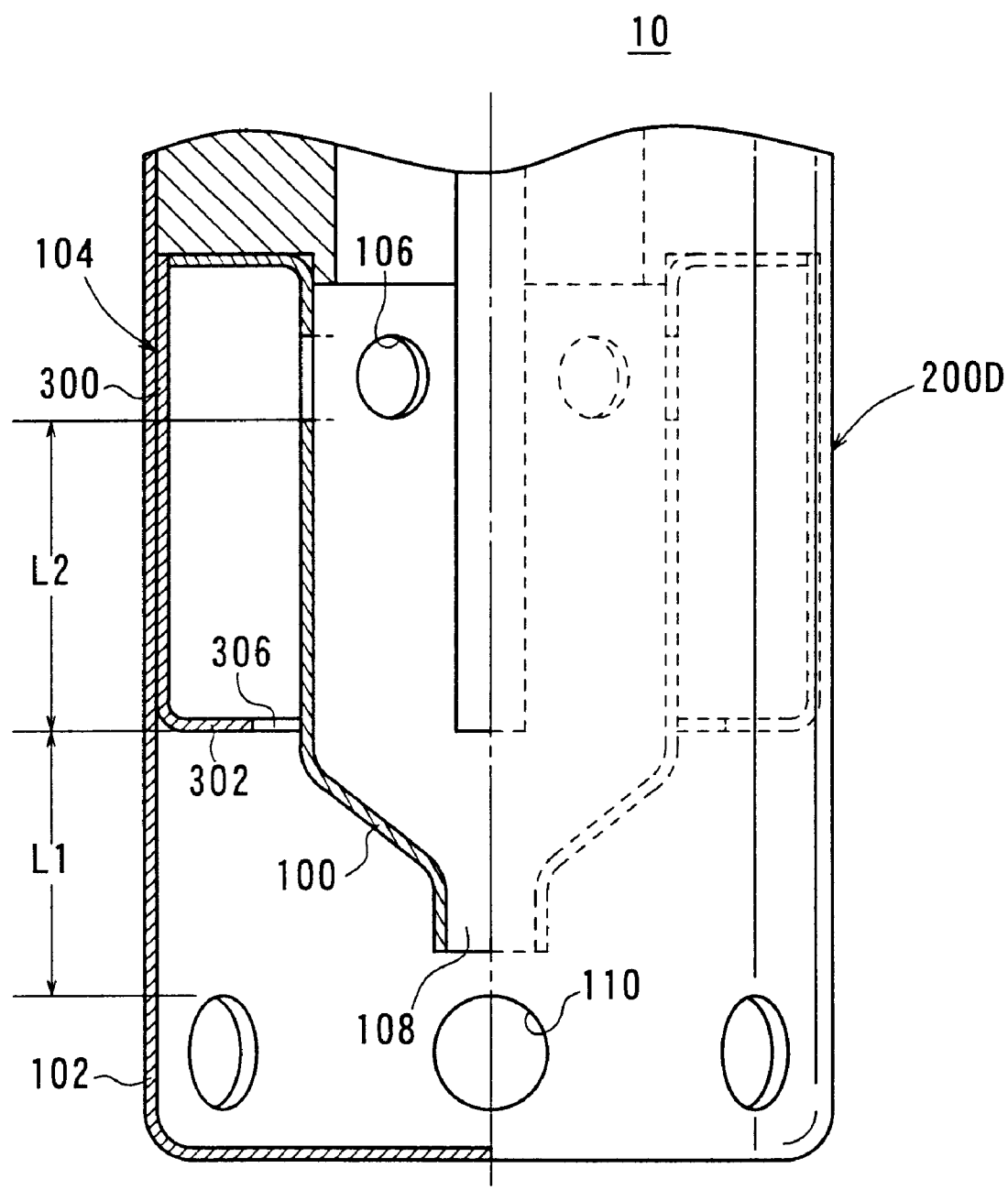
FIG. 7 shows a sectional view illustrating, with partial omission, a gas sensor according to an embodiment of the present invention attached with a protective cover concerning a fourth specified embodiment.

As shown in FIG. 7, the protective cover 200D concerning the fourth specified embodiment is constructed in approximately the same manner as the protective cover 200C concerning the third specified embodiment. However, the former is different from the latter in that the forward end of the inner protective cover 100 is throttled to form an inner gas discharge hole 108 having a diameter of about 2 mm at its forward end, and that the intermediate protective cover 104 is integrally formed by a cylindrical section 300 contacting with the inner circumferential wall of the outer protective cover 102, and a bent section 302 bent inwardly at a lower portion of the cylindrical section 300. The diameter of the inner gas-introducing hole 106 of the inner protective cover 100 is about 1.4 mm. The diameter of the outer gas-introducing hole 110 of the outer protective cover 102 is about 2.0 mm.

Figure 8:
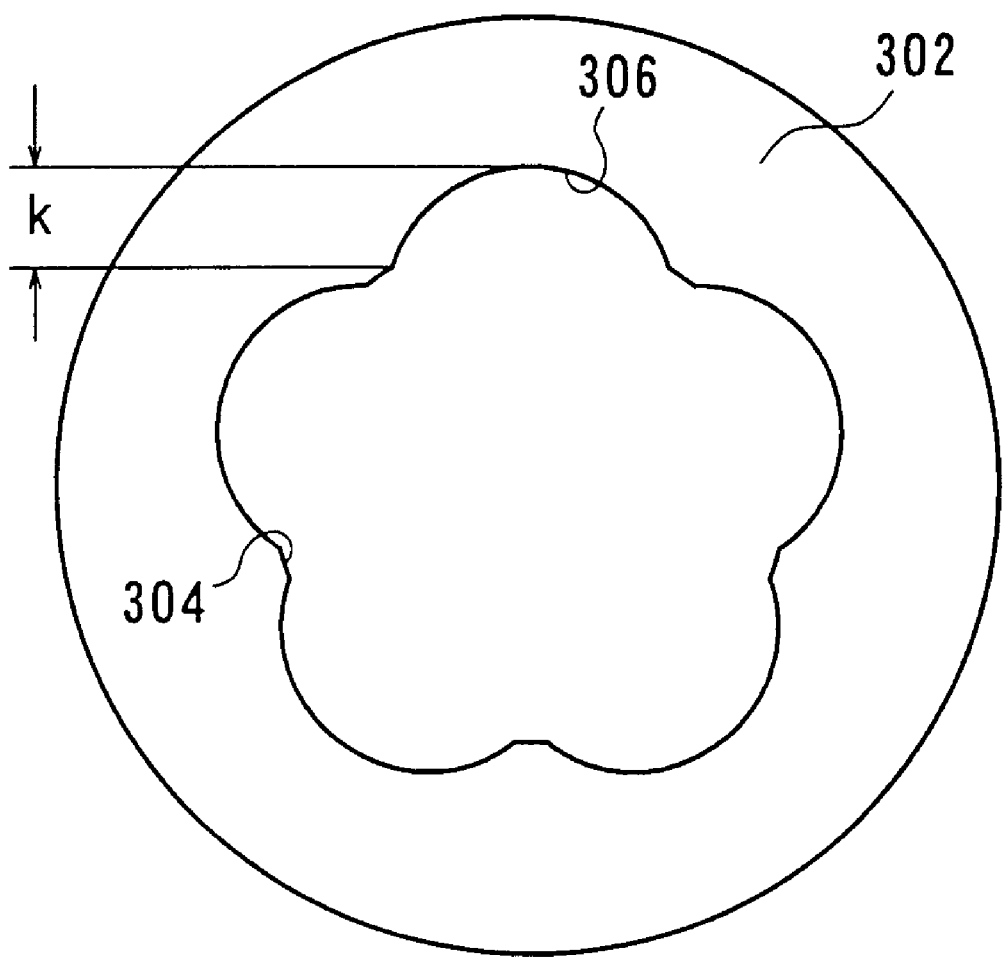
FIG. 8 shows an arrangement of a bent section of the protective cover concerning the fourth modified embodiment, as viewed from a front end side of the protective cover.

As shown in FIG. 8, the bent section 302 is formed with a through-hole 304 for inserting the inner protective cover 100 therethrough. Further, cutouts 306, which have, for example, a semi-elliptical configuration, are arranged, for example, at equally divided five positions around the through-hole 304. The cutouts 306, which have a depth k of about 0.8 mm, constitute intermediate gas-introducing holes 130 of the intermediate protective cover 104.

The most adjacent spacing distance L1 in the axial direction between the outer gas-introducing hole 110 and the cutout 306 is about 5.5 mm. The most adjacent spacing distance L2 in the axial direction between the cutout 306 and the inner gas-introducing hole 106 is about 6.3 mm.

Also in this case, it is possible to effectively avoid the adhesion of condensed water (so-called water splash) which would be otherwise caused when the engine is started. Further, the diffusion rate-limiting of the measurement gas can be decreased to be as small as possible, and it is possible to obtain quick response performance.

Next, a protective cover 200E concerning a fifth specified embodiment will be explained with reference to FIGS. 9 and 10. Components or parts corresponding to those shown in FIG. 7 are designated by the same reference numerals, duplicate explanation of which will be omitted.

Figure 9:
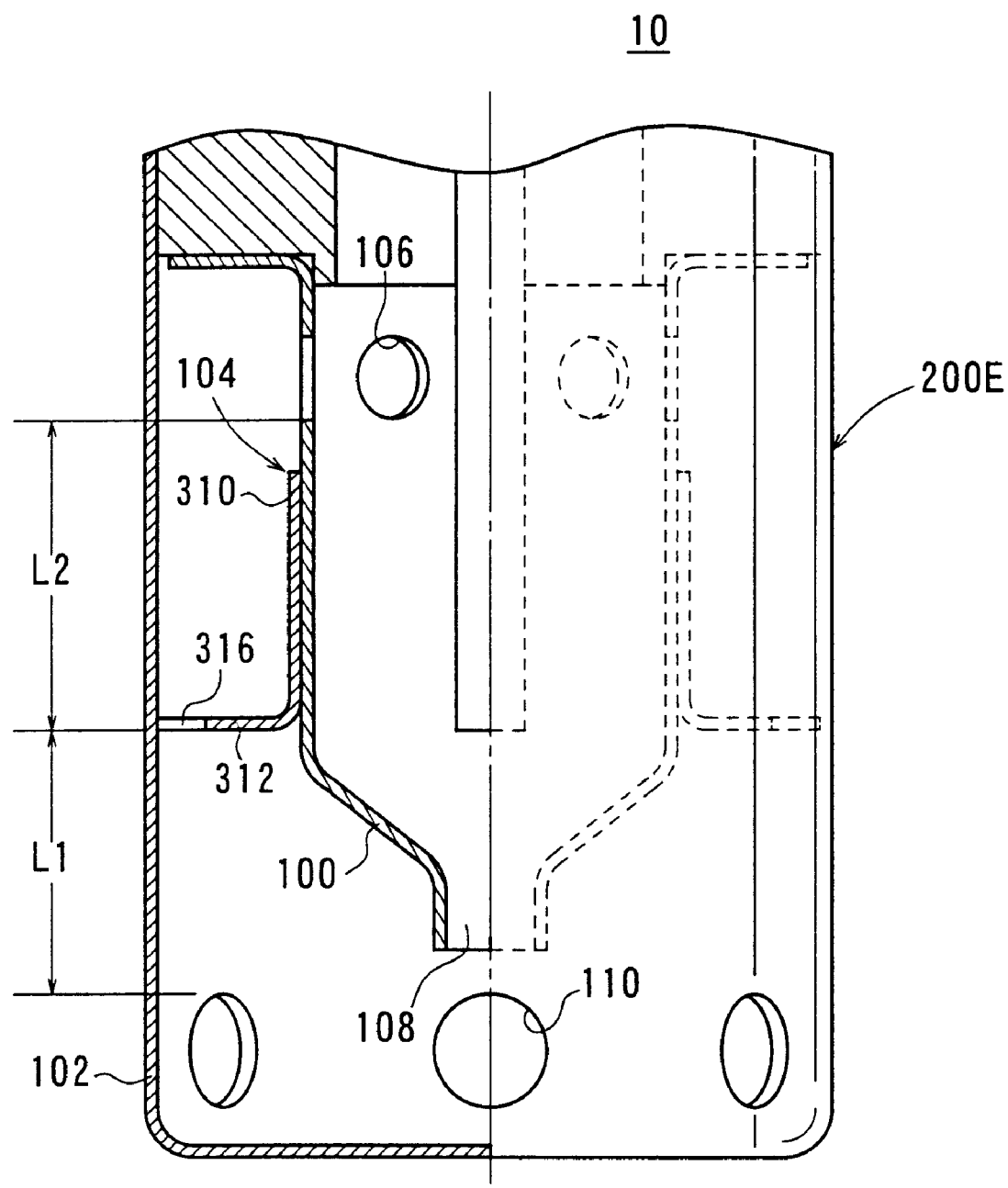
FIG. 9 shows a sectional view illustrating, with partial omission, a gas sensor according to an embodiment of the present invention attached with a protective cover concerning a fifth specified embodiment.

As shown in FIG. 9, the protective cover 200E concerning the fifth specified embodiment is constructed in approximately the same manner as the protective cover 200D concerning the fourth specified embodiment. However, the former is different from the latter in that the intermediate protective cover 104 is integrally formed by a cylindrical section 310 contacting with the outer circumferential wall of the inner protective cover 100, and a flange 312 bent outwardly at a lower portion of the cylindrical section 310.

Figure 10:
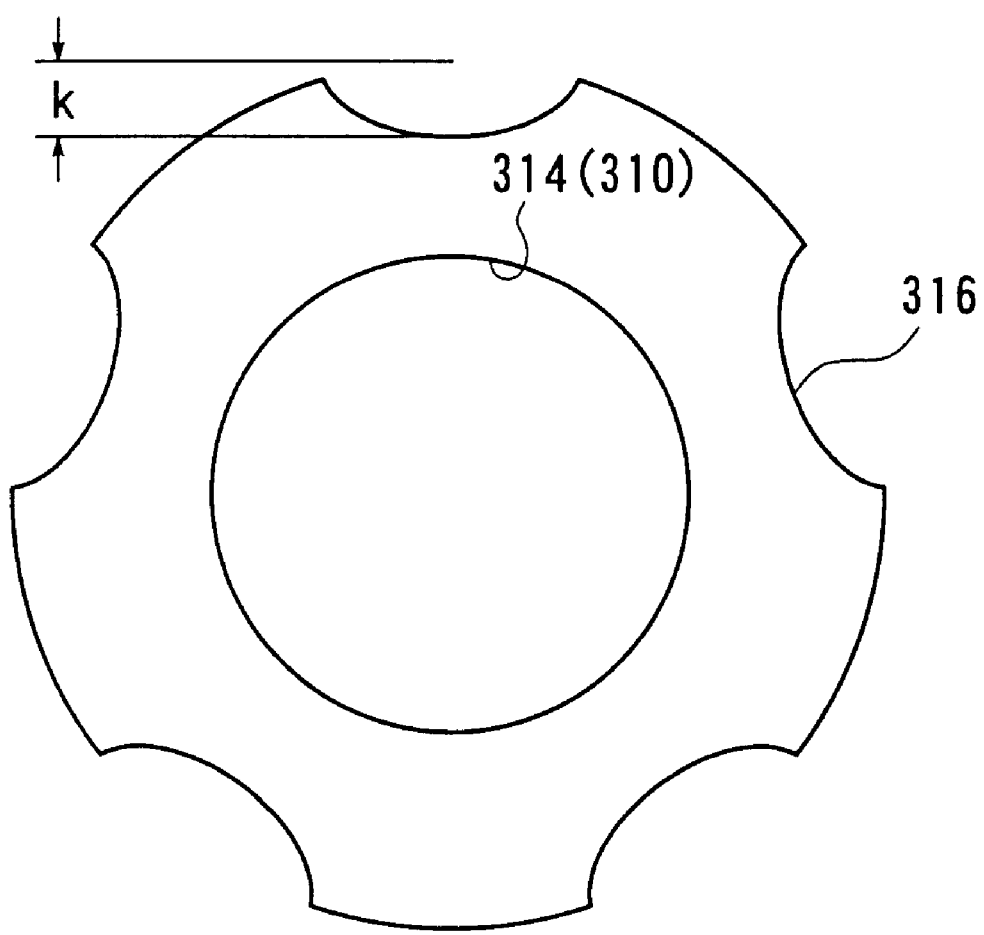
FIG. 10 shows an arrangement of a bent section of the protective cover concerning the fifth modified embodiment, as viewed from a front end side of the protective cover.

As shown in FIG. 10, the cylindrical section 310 is formed with a hollow section 314 for inserting the inner protective cover 100 therethrough. Further, cutouts 316, which have, for example, a semi-elliptical configuration, are arranged, for example, at equally divided five positions at the circumferential end edge of the flange 312. The cutouts 316, which have a depth k of about 0.8 mm, constitute intermediate gas-introducing holes 130 of the intermediate protective cover 104.

The most adjacent spacing distance L1 in the axial direction between the outer gas-introducing hole 110 and the cutout 316 is about 5.5 mm. The most adjacent spacing distance L2 in the axial direction between the cutout 316 and the inner gas-introducing hole 106 is about 6.3 mm.

Also in this case, it is possible to effectively avoid the adhesion of condensed water (so-called water splash) which would be otherwise caused when the engine is started. Further, the diffusion rate-limiting of the measurement gas can be decreased to be as small as possible, and it is possible to obtain quick response performance.

Two illustrative experiments (conveniently referred to as "first and second illustrative experiments") will now be described. In the first illustrative experiment, the frequency to repeat the rich and the lean was measured by using gas sensors concerning Working Examples 1 to 7 and gas sensors concerning Comparative Examples 1 and 2 as controller sensors respectively under a condition of a 2.0-liter gasoline engine (1800 rpm·4 kgm).

Working Example 1 is constructed in approximately the same manner as the protective cover 200B according to the second specified embodiment. Working Example 2 is constructed in approximately the same manner as the protective cover 200C according to the third specified embodiment. Working Examples 3 to 5 are constructed in approximately the same manner as the protective cover 200A according to the first specified embodiment. Especially, in Working Example 3, the total of the most adjacent spacing distance L1 and the most adjacent spacing distance L2 is 18.4 mm. In Working Example 4, the total of the most adjacent spacing distance L1 and the most adjacent spacing distance L2 is 17.4 mm. In Working Example 5, the total of the most adjacent spacing distance L1 and the most adjacent spacing distance L2 is 16.4 mm. Working Example 6 is constructed in approximately the same manner as the protective cover 200D according to the fourth specified embodiment. Working Example 7 is constructed in approximately the same manner as the protective cover 200E according to the fifth specified embodiment.

Figure 11:
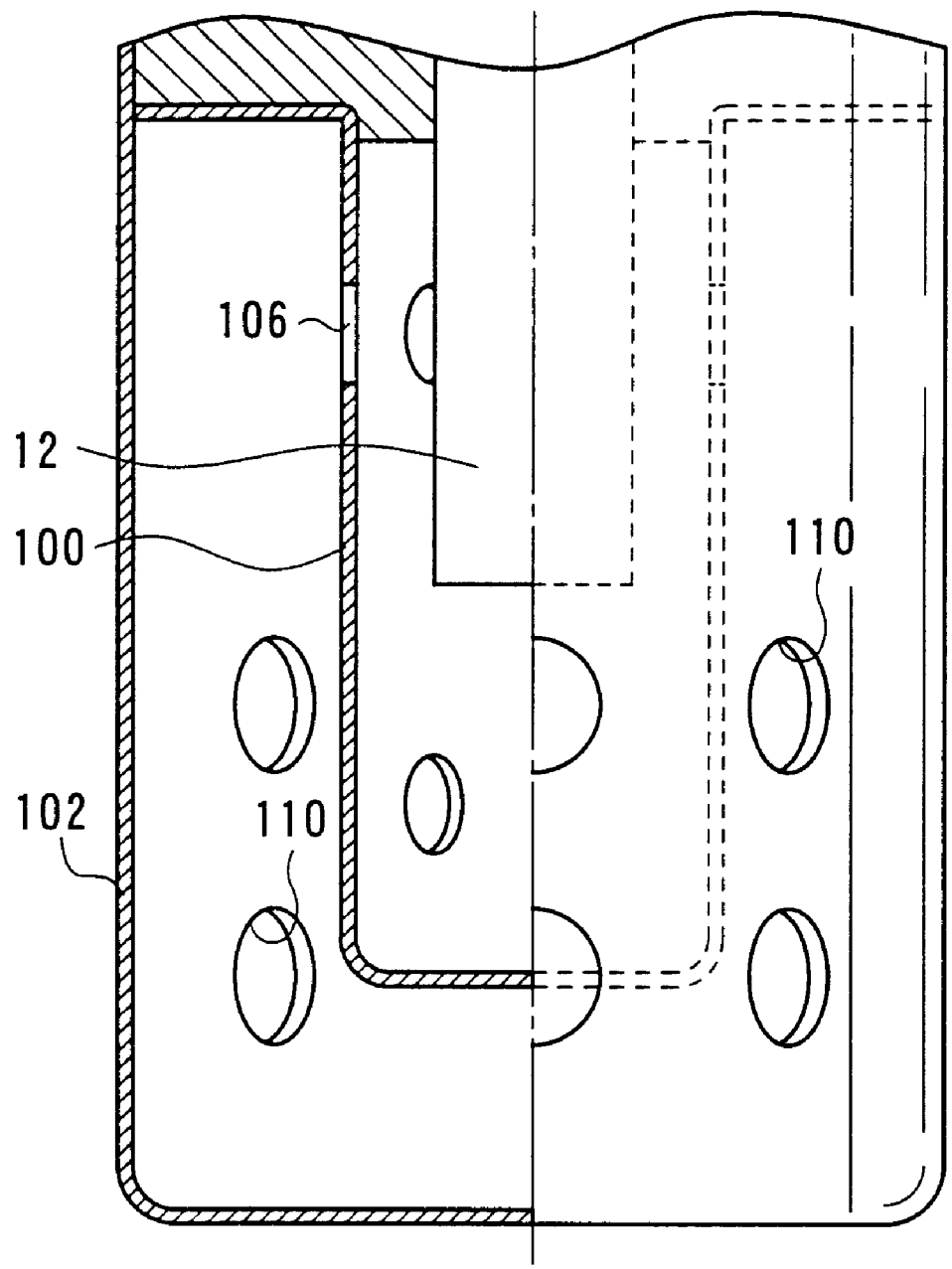
FIG. 11 shows an arrangement of Comparative Example 1.

On the other hand, Comparative Example 1 is constructed as follows as shown in FIG. 11. That is, the intermediate protective cover 104 is removed from the protective cover 200A concerning the first specified embodiment to give a double structure comprising the outer protective cover 102 and the inner protective cover 100. Further, inner gas-introducing holes 106 are formed at positions of the inner protective cover 100 opposed to the sensor element 12. The most adjacent spacing distance in the axial direction between the inner gas-introducing hole 106 and the outer gas-introducing hole 110 formed at the outer protective cover 102 is shortened to improve the response performance.

Figure 12:
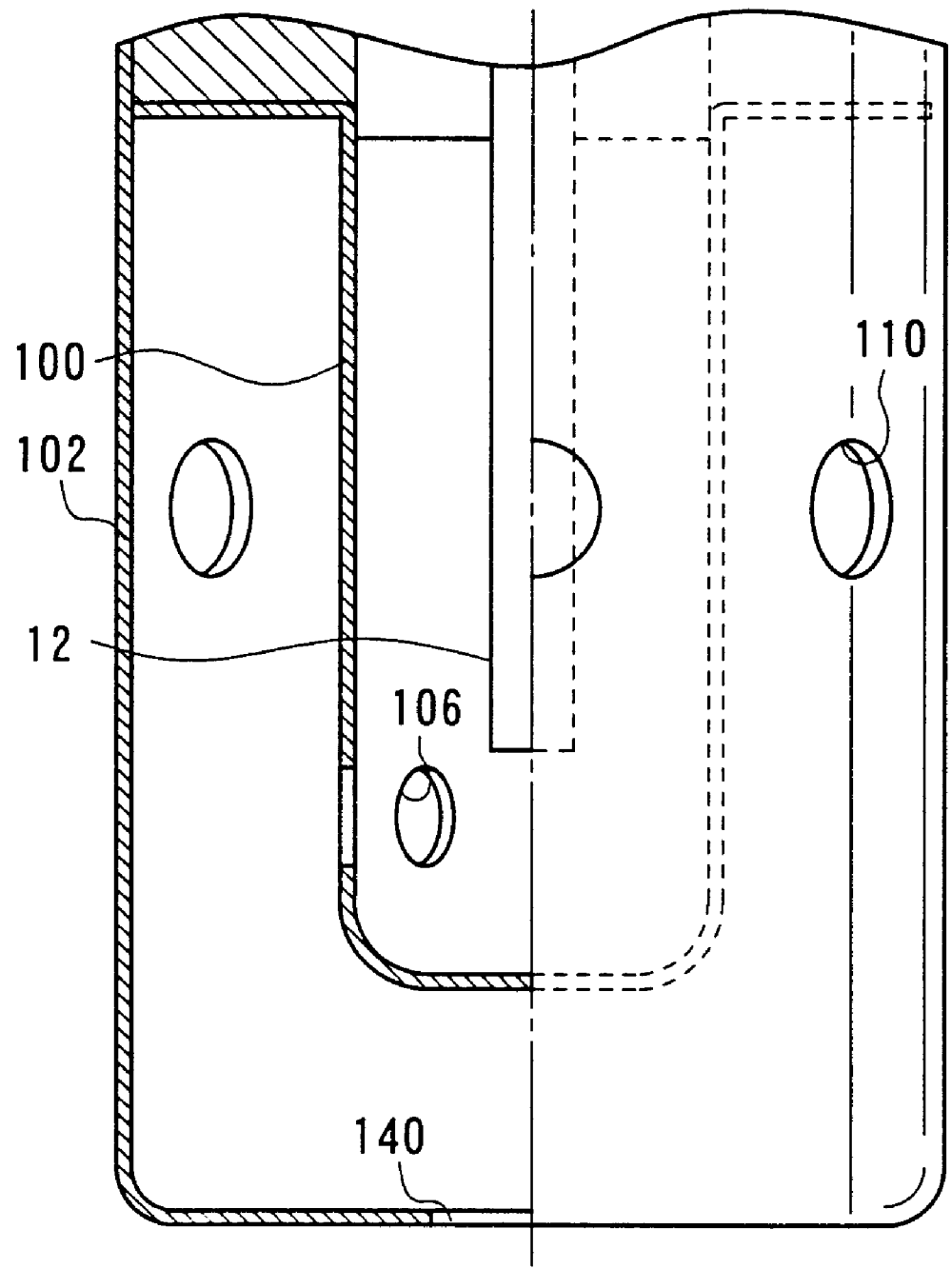
FIG. 12 shows an arrangement of Comparative Example 2.

Comparative Example 2 is constructed as follows as shown in FIG. 12. That is, the intermediate protective cover 104 is removed from the protective cover 200A concerning the first specified embodiment to give a double structure comprising the outer protective cover 102 and the inner protective cover 100. Further, in order to improve the water scattering resistance, inner gas-introducing holes 106 are formed at positions of the side circumferential surface of the inner protective cover 100 not opposed to the sensor element 12. Outer gas-introducing holes 110 are formed at positions of the side circumferential surface of the outer protective cover 102 deviated rearwardly as compared with the inner gas-introducing holes 106. A gas discharge hole 140 is formed at the bottom of the outer protective cover 102.

Figure 13:
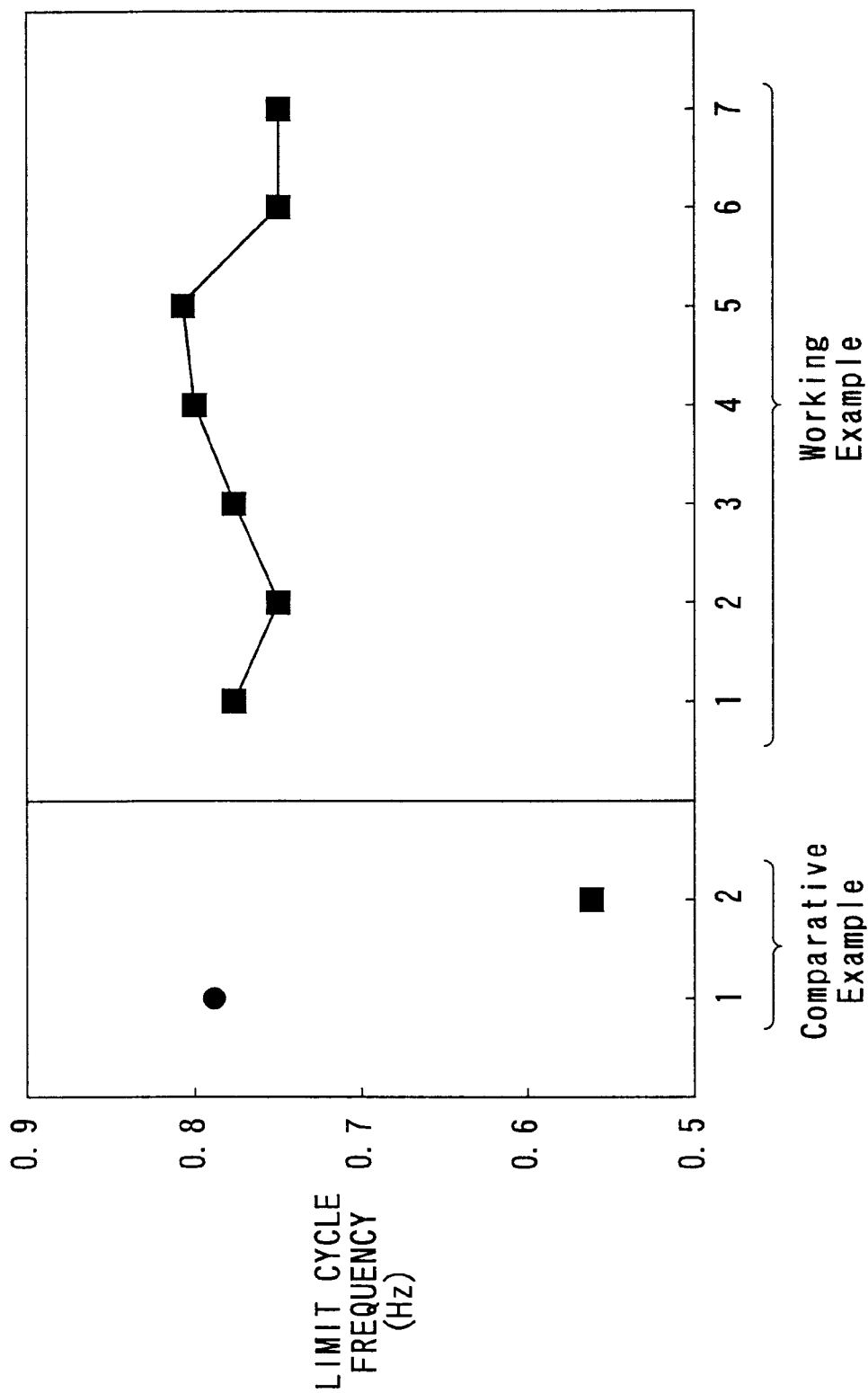
FIG. 13 shows a characteristic illustrating results of a first illustrative experiment (experiment to investigate the response performance)

Results of the first illustrative experiment are shown in FIG. 13. According to the results, it is understood that Comparative Example 1 has a large limit cycle frequency of 0.79 Hz, and the response is quick. On the other hand, Comparative Example 2 has the structure considering the water scattering resistance, in which the limit cycle frequency is 0.56 Hz that is small, and the response is slow.

In Working Examples 1 to 7, the limit cycle frequency is not less than 0.75 Hz. It is understood that the response performance is improved owing to the provision of the intermediate protective cover 104.

According to the results of 0.78 Hz for Working Example 1, 0.75 Hz for Working Example 2, 0.78 Hz for Working Example 3, 0.8 Hz for Working Example 4, 0.81 Hz for Working Example 5, 0.75 Hz for Working Example 6, and 0.75 Hz for Working Example 7, the following fact is comprehensible. That is, when the structure, in which the bent section 130 is integrally formed with the flange 116, is adopted as in the protective cover 200C concerning the third specified embodiment, it is possible to obtain the frequency which is approximately the same as or not less than the limit cycle frequency of 0.79 Hz in Comparative Example 1 in which only the response performance is intended to be improved. The structure as described above is advantageous in view of the improvement in response performance.

In the second illustrative experiment, observation was made for the situation of water splash and the degree of occurrence of crack in the sensor element 12 in relation to the gas sensors concerning Working Examples 1 to 7 and the gas sensors concerning Comparative Examples 1 and 2.

Specifically, the water splash situation was observed as follows. That is, 100 cc of water, which was colored with black ink or the like, was pooled at a downstream portion in the vicinity of the catalyst. After the gas sensor was warmed up for 1.5 minute, the engine was started to maintain the idle state for 10 seconds. After that, the racing at 5000 rpm was carried out once to evaluate the adhesion state of condensed water to the sensor element 12 so that the evaluation was made with ten grades.

Whether or not the water adhered to the sensor element 12 was judged by visual observation. The water droplet adhesion ratio was estimated.

The degree of occurrence of crack in the sensor element 12 was observed as follows. That is, a predetermined number of samples were prepared for each of Comparative Examples and each of Working Examples. When any crack occurred in the sample sensor element, "1" was counted and added. An obtained added value was evaluated with ten grades.

Results of the second illustrative experiment are shown in FIG. 14. In FIG. 14, n/10 concerning the water splash situation is an index to indicate the degree of adhesion of condensed water to the entire sensor element 12. It is indicated that the more approximate to 10 the number of n is, the larger the amount of adhered water is. The following expression is collectively adopted. That is, the larger the number of n is, the worse the water splash situation is, while the smaller the number of n is, the better the water splash situation is. Therefore, 10/10 corresponds to a state in which the condensed water adheres to the entire sensor element 12, indicating that the water splash situation is the worst. On the other hand, 0/10 corresponds to a state in which no condensed water adheres to the sensor element 12 at all, indicating that the water splash situation is the best.

Further, m/10 concerning the water splash situation indicates the degree (probability) of occurrence of the crack in the sensor element 12. It is indicated that the larger the value of m is, the more probably the crack occurs. No occurrence of crack is indicated by 0/10.

According to the results shown in FIG. 14, the following fact is comprehensible. That is, in Comparative Example 1, the water splash situation is 10/10, the adhesion of condensed water appears over the entire sensor element 12, and the crack occurs in the sensor element 12, because Comparative Example 1 is principally constructed in order to improve the response performance.

In Comparative Example 2, the water splash situation is 0/10, no condensed water adheres, and no crack occurs in the sensor element 12 as well. This is because the protective cover of Comparative Example 2 is principally constructed in order to improve the water scattering resistance. The response performance is lowered, as also understood from the first illustrative experiment (see FIG. 13).

As for Working Examples 1 to 7, the water splash situation is 3/10 to 4/10 in Working Example 1, Working Example 6, and Working Example 7, wherein the water splash situation is somewhat deteriorated. However, judging from an overall viewpoint, it is understood that the water splash situation is good, and the water scattering resistance is improved. No crack occurs in the sensor element 12.

As described above, in Working Examples 1 to 7, both of the improvement in water scattering resistance and the improvement in response performance, which are contrary to one another, can be simultaneously realized.

Next, a protective cover 200F concerning a sixth specified embodiment will be explained with reference to FIG. 15. Components or parts corresponding to those shown in FIG. 1 are designated by the same reference numerals, duplicate explanation of which will be omitted.

Figure 15:
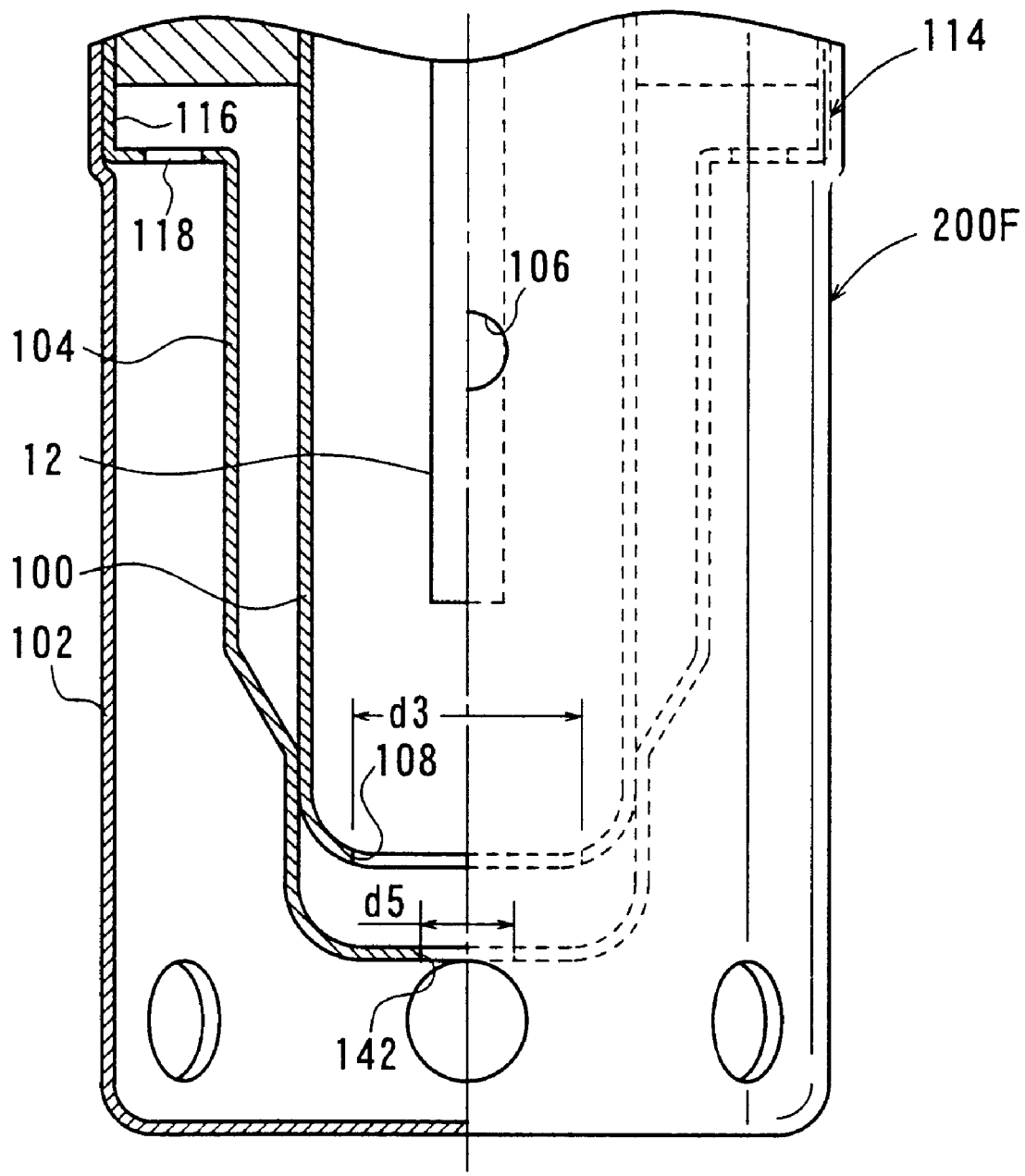
FIG. 15 shows a sectional view illustrating, with partial omission, a gas sensor according to an embodiment of the present invention attached with a protective cover concerning a sixth specified embodiment.

As shown in FIG. 15, the protective cover 200F concerning the sixth specified embodiment is constructed in approximately the same manner as the protective cover 200A concerning the first specified embodiment. However, the former is different from the latter in that the intermediate protective cover 104 is formed to have a bottom-equipped cylindrical configuration to cover the forward end portion of the inner protective cover 100 with the forward end portion of the intermediate protective cover 104.

An intermediate gas discharge hole 142 having a diameter d5=about 2.0 mm is formed at a central portion of the forward end surface of the intermediate protective cover 104. The diameter d3 of the inner gas discharge hole 108 of the inner protective cover 100 is about 4.5 mm.

Also in this case, it is possible to effectively avoid the adhesion of condensed water (so-called water splash) which would be otherwise caused when the engine is started.

Further, the diffusion rate-limiting of the measurement gas can be decreased to be as small as possible, and it is possible to obtain quick response performance.

It is a matter of course that the gas sensor according to the present invention is not limited to the embodiments described above, which may be embodied in other various forms without deviating from the gist or essential characteristics of the present invention.

As explained above, according to the gas sensor concerning the present invention, the diffusion rate-limiting of the gas can be decreased to be as small as possible, and it is possible to simultaneously realize the high water scattering resistance and the quick response, with the protective cover having the water scattering resistance.

What is claimed is:

1. A gas sensor comprising a sensor element for measuring a predetermined gas component contained in an introduced measurement gas, and a protective cover arranged to surround said sensor element, wherein said protective cover includes:

an inner protective cover for covering at least a forward end portion of said sensor element;

an outer protective cover for covering said inner protective cover; and an intermediate protective cover installed between said inner protective cover and said outer protective cover, and wherein:

said inner protective cover is formed to have a bottom-equipped cylindrical configuration with an inner gas-introducing hole which is formed at a position opposed to said sensor element and with an inner gas discharge hole which is formed at a bottom portion;

said outer protective cover is formed to have a bottom-equipped cylindrical configuration with an outer gas-introducing hole which is disposed at a position not opposed to said inner gas-introducing hole of said inner protective cover; and said intermediate protective cover has an intermediate gas-introducing hole which is disposed at a position not opposed to said inner gas-introducing hole of said inner protective cover and said outer gas-introducing hole of said outer protective cover.

2. The gas sensor according to claim 1, wherein a total of a most adjacent spacing distance in an axial direction between said outer gas-introducing hole and said intermediate gas-introducing hole and a most adjacent spacing distance in said axial direction between said intermediate gas-introducing hole and said inner gas-introducing hole is at least not less than 10 mm.

3. The gas sensor according to claim 1, wherein gaps for avoiding accumulation of water due to boundary tension are provided between said outer protective cover and said intermediate protective cover in a radial direction and between said outer protective cover and said inner protective cover in said radial direction.

4. The gas sensor according to claim 1, wherein said intermediate protective cover is formed to have a cylindrical configuration with an opening which is formed at a front portion thereof for inserting said inner protective cover thereinto and with a flange which is disposed at a rear portion thereof for making abutment against an inner wall of said outer protective cover.

5. The gas sensor according to claim 4, wherein said intermediate gas-introducing hole is formed at said flange of said intermediate protective cover.

6. The gas sensor according to claim 1, wherein said intermediate protective cover is formed to have a bottom-equipped cylindrical configuration with an intermediate gas discharge hole which is formed at a bottom portion thereof.

7. The gas sensor according to claim 6, wherein a part of said outer gas-introducing hole of said outer protective cover is provided at a side surface portion of said outer protective cover between said inner gas discharge hole or said intermediate gas discharge hole and a bottom of said outer protective cover.

* * * * *